(12) United States Patent
Mayberry et al.

(10) Patent No.: US 8,523,931 B2
(45) Date of Patent: Sep. 3, 2013

(54) DUAL CONCENTRIC GUIDEWIRE AND METHODS OF BIFURCATED GRAFT DEPLOYMENT

(75) Inventors: Kevin J. Mayberry, Mission Viejo, CA (US); Trinh V. Pham, Westminster, CA (US); Brian C. Gray, Lake Forest, CA (US)

(73) Assignee: Endologix, Inc., Irvine, CA (US)

(*) Notice: Subject to any disclaimer, the term of this patent is extended or adjusted under 35 U.S.C. 154(b) by 1219 days.

(21) Appl. No.: 11/623,022

(22) Filed: Jan. 12, 2007

(65) Prior Publication Data

US 2008/0172122 A1    Jul. 17, 2008

(51) Int. Cl.
*A61F 2/06* (2013.01)

(52) U.S. Cl.
USPC .......................................... 623/1.11; 623/1.35

(58) Field of Classification Search
USPC .................... 623/1.11, 1.12, 1.23, 1.13, 1.16, 623/1.35; 606/108, 198, 200; 600/585
See application file for complete search history.

(56) References Cited

U.S. PATENT DOCUMENTS

| | | |
|---|---|---|
| 2,127,903 A | 8/1938 | Bowen |
| 2,437,542 A | 5/1944 | Krippendorf |
| 2,845,959 A | 8/1958 | Sidebotham |
| 2,990,605 A | 7/1961 | Demsyk |
| 3,029,819 A | 4/1962 | Starks |
| 3,096,560 A | 7/1963 | Liebig |
| 3,805,301 A | 4/1974 | Liebig |
| 3,994,149 A | 11/1976 | Dahlman |
| 4,497,074 A | 2/1985 | Rey et al. |
| 4,501,263 A | 2/1985 | Harbuck |
| 4,503,568 A | 3/1985 | Madras |
| 4,580,568 A | 4/1986 | Gianturco |
| 4,592,754 A | 6/1986 | Gupte et al. |
| 4,617,932 A | 10/1986 | Kornberg |
| 4,756,307 A | 7/1988 | Crowninshield |
| 4,800,882 A | 1/1989 | Gianturco |
| 4,816,028 A | 3/1989 | Kapadia et al. |
| 4,840,940 A | 6/1989 | Sottiurai |

(Continued)

FOREIGN PATENT DOCUMENTS

| | | |
|---|---|---|
| DE | 100 17 147 A1 | 10/2001 |
| DE | 10017147 A1 | 10/2001 |

(Continued)

OTHER PUBLICATIONS

Defintion of "mounted", Dictionary.com, retrieved Nov. 18, 2010 from http://dictionary.com/browse/mounted.*

(Continued)

*Primary Examiner* — Thomas McEvoy

(74) *Attorney, Agent, or Firm* — Knobbe, Martens, Olson & Bear LLP

(57) ABSTRACT

A guidewire assembly for use in deploying a bifurcated endoluminal vascular prosthesis that has a main graft portion and at least a first branch graft portion The guidewire assembly include a hollow guidewire sheath having a restraint mechanism, such as a tubular sheath, for constraining a branch graft portion of the vascular prosthesis and an inner core wire that is slidably insertable into a central lumen of the hollow guidewire sheath. In use, the guidewire assembly may be used with a deployment catheter to deploy the bifurcated vascular prosthesis and leave the inner core wire in position in the patient's aorta, extending through the main graft portion of the vascular prosthesis.

22 Claims, 15 Drawing Sheets

(56) References Cited

U.S. PATENT DOCUMENTS

| | | | |
|---|---|---|---|
| 4,856,516 A | 8/1989 | Hillstead | |
| 4,878,906 A | 11/1989 | Lindemann et al. | |
| 4,907,336 A | 3/1990 | Gianturco | |
| 4,922,905 A | 5/1990 | Strecker | |
| 4,981,478 A | 1/1991 | Evard et al. | |
| 4,981,947 A | 1/1991 | Tomagou et al. | |
| 4,994,071 A | 2/1991 | MacGregor | |
| 5,019,090 A | 5/1991 | Pinchuk | |
| 5,035,706 A | 7/1991 | Giantureo et al. | |
| 5,064,435 A | 11/1991 | Porter | |
| 5,078,726 A | 1/1992 | Kreamer | |
| 5,104,399 A | 4/1992 | Lazarus | |
| 5,108,424 A | 4/1992 | Hoffman, Jr. et al. | |
| 5,116,349 A | 5/1992 | Aranyi | |
| 5,123,917 A | 6/1992 | Lee | |
| 5,133,732 A | 7/1992 | Wiktor | |
| 5,135,535 A | 8/1992 | Kramer | |
| 5,135,536 A | 8/1992 | Hillstead | |
| 5,156,619 A | 10/1992 | Ehrenfeld | |
| 5,178,634 A | 1/1993 | Ramos Martinez | |
| 5,195,978 A | 3/1993 | Schiffer | |
| 5,197,976 A | 3/1993 | Herweck et al. | |
| 5,201,757 A | 4/1993 | Heyn et al. | |
| 5,211,658 A | 5/1993 | Clouse | |
| 5,256,141 A | 10/1993 | Gencheff et al. | |
| 5,263,932 A | 11/1993 | Jang | |
| 5,275,622 A | 1/1994 | Lazarus et al. | |
| 5,282,478 A * | 2/1994 | Fleischhaker et al. | 600/585 |
| 5,282,824 A | 2/1994 | Gianturco | |
| 5,282,860 A | 2/1994 | Matsuno et al. | |
| 5,304,200 A | 4/1994 | Spaulding | |
| 5,314,444 A | 5/1994 | Gianturco | |
| 5,314,472 A | 5/1994 | Fontaine | |
| 5,316,023 A | 5/1994 | Palmaz et al. | |
| 5,320,602 A | 6/1994 | Karpiel | |
| 5,330,500 A | 7/1994 | Song | |
| 5,342,387 A | 8/1994 | Summers | |
| 5,354,308 A | 10/1994 | Simon et al. | |
| 5,360,443 A | 11/1994 | Barone et al. | |
| 5,366,504 A | 11/1994 | Andersen et al. | |
| 5,370,683 A | 12/1994 | Fontaine | |
| 5,387,235 A | 2/1995 | Chuter | |
| 5,397,355 A | 3/1995 | Marin et al. | |
| 5,405,377 A | 4/1995 | Cragg | |
| 5,415,178 A * | 5/1995 | Hsi et al. | 600/585 |
| 5,415,664 A | 5/1995 | Pinchuk | |
| 5,423,886 A | 6/1995 | Arru et al. | |
| 5,425,765 A | 6/1995 | Tiefenbrun et al. | |
| 5,443,477 A | 8/1995 | Marin et al. | |
| 5,443,498 A | 8/1995 | Fontaine | |
| 5,443,500 A | 8/1995 | Sigwart | |
| 5,456,713 A | 10/1995 | Chuter | |
| 5,458,615 A | 10/1995 | Klemm et al. | |
| 5,462,530 A | 10/1995 | Jang | |
| 5,464,450 A | 11/1995 | Buscemi et al. | |
| 5,484,444 A | 1/1996 | Braunschweiler et al. | |
| 5,489,295 A | 2/1996 | Piplani et al. | |
| 5,496,365 A | 3/1996 | Sgro | |
| 5,507,767 A | 4/1996 | Maeda et al. | |
| 5,507,769 A | 4/1996 | Marin et al. | |
| 5,507,771 A | 4/1996 | Gianturco | |
| 5,522,880 A | 6/1996 | Barone et al. | |
| 5,522,881 A | 6/1996 | Lentz | |
| 5,522,883 A | 6/1996 | Slater et al. | |
| 5,545,118 A | 8/1996 | Romanauskas | |
| 5,545,211 A | 8/1996 | An et al. | |
| 5,554,181 A | 9/1996 | Das | |
| 5,562,697 A | 10/1996 | Christiansen | |
| 5,562,726 A | 10/1996 | Chuter | |
| 5,562,728 A | 10/1996 | Lazarus et al. | |
| 5,571,173 A | 11/1996 | Parodi | |
| 5,575,816 A | 11/1996 | Rudnick et al. | |
| 5,575,818 A | 11/1996 | Pinchuk | |
| 5,578,071 A | 11/1996 | Parodi | |
| 5,578,072 A | 11/1996 | Barone et al. | |
| 5,591,197 A | 1/1997 | Orth et al. | |
| 5,591,198 A | 1/1997 | Boyle et al. | |
| 5,591,229 A | 1/1997 | Parodi | |
| 5,591,230 A | 1/1997 | Horn et al. | |
| 5,593,417 A | 1/1997 | Rhodes | |
| 5,604,435 A | 2/1997 | Foo et al. | |
| 5,607,445 A | 3/1997 | Summers | |
| 5,609,625 A | 3/1997 | Piplani et al. | |
| 5,609,627 A | 3/1997 | Goicoechea et al. | |
| 5,609,628 A | 3/1997 | Keranen | |
| 5,628,783 A | 5/1997 | Quiachon et al. | |
| 5,628,786 A | 5/1997 | Banas et al. | |
| 5,628,788 A | 5/1997 | Pinchuk | |
| 5,630,829 A | 5/1997 | Lauterjung | |
| 5,630,830 A | 5/1997 | Verbeek | |
| 5,632,763 A | 5/1997 | Glastra | |
| 5,632,772 A | 5/1997 | Alcime et al. | |
| 5,639,278 A | 6/1997 | Dereume et al. | |
| 5,641,373 A | 6/1997 | Shannon et al. | |
| 5,643,171 A | 7/1997 | Bradshaw et al. | |
| 5,643,278 A | 7/1997 | Wijay | |
| 5,647,857 A | 7/1997 | Anderson et al. | |
| 5,649,952 A | 7/1997 | Lam | |
| 5,651,174 A | 7/1997 | Schwartz et al. | |
| 5,653,727 A | 8/1997 | Wiktor | |
| 5,653,743 A | 8/1997 | Martin | |
| 5,653,746 A | 8/1997 | Schmitt | |
| 5,653,747 A | 8/1997 | Dereume | |
| 5,662,580 A | 9/1997 | Bradshaw et al. | |
| 5,662,614 A | 9/1997 | Edoga | |
| 5,662,700 A | 9/1997 | Lazarus | |
| 5,662,701 A | 9/1997 | Plaia et al. | |
| 5,662,702 A | 9/1997 | Keranen | |
| 5,662,703 A | 9/1997 | Yurek et al. | |
| 5,665,115 A | 9/1997 | Cragg | |
| 5,669,880 A | 9/1997 | Solar | |
| 5,669,924 A | 9/1997 | Shaknovich | |
| 5,674,241 A | 10/1997 | Bley et al. | |
| 5,674,276 A | 10/1997 | Andersen et al. | |
| 5,676,685 A | 10/1997 | Razavi | |
| 5,676,696 A | 10/1997 | Marcade | |
| 5,676,697 A | 10/1997 | McDonald | |
| 5,679,400 A | 10/1997 | Tuch | |
| 5,681,345 A | 10/1997 | Euteneuer | |
| 5,681,346 A | 10/1997 | Orth et al. | |
| 5,683,448 A | 11/1997 | Cragg | |
| 5,683,449 A | 11/1997 | Marcade | |
| 5,683,450 A | 11/1997 | Goicoechea et al. | |
| 5,683,451 A | 11/1997 | Lenker et al. | |
| 5,683,452 A | 11/1997 | Barone et al. | |
| 5,683,453 A | 11/1997 | Palmaz | |
| 5,690,642 A | 11/1997 | Osborne et al. | |
| 5,690,643 A | 11/1997 | Wijay | |
| 5,690,644 A | 11/1997 | Yurek et al. | |
| 5,693,066 A | 12/1997 | Rupp et al. | |
| 5,693,084 A | 12/1997 | Chuter | |
| 5,693,086 A | 12/1997 | Goicoechea et al. | |
| 5,693,087 A | 12/1997 | Parodi | |
| 5,693,088 A | 12/1997 | Lazarus | |
| 5,695,516 A | 12/1997 | Fischell et al. | |
| 5,695,517 A | 12/1997 | Marin et al. | |
| 5,697,948 A | 12/1997 | Marin et al. | |
| 5,709,703 A | 1/1998 | Lukic et al. | |
| 5,713,917 A | 2/1998 | Leonhardt et al. | |
| 5,716,365 A | 2/1998 | Goicoechea et al. | |
| 5,716,393 A | 2/1998 | Lindenberg et al. | |
| 5,718,724 A | 2/1998 | Goicoechea et al. | |
| 5,718,973 A | 2/1998 | Lewis et al. | |
| 5,720,735 A | 2/1998 | Dorros | |
| 5,720,776 A | 2/1998 | Chuter et al. | |
| 5,723,004 A | 3/1998 | Dereume et al. | |
| 5,733,325 A | 3/1998 | Robinson et al. | |
| 5,746,766 A | 5/1998 | Edoga | |
| 5,746,776 A | 5/1998 | Smith et al. | |
| 5,749,880 A | 5/1998 | Banas et al. | |
| 5,755,770 A | 5/1998 | Ravenscroft | |
| 5,755,771 A | 5/1998 | Penn et al. | |
| 5,755,777 A | 5/1998 | Chuter | |
| 5,769,885 A | 6/1998 | Quiachon et al. | |

| | | | | | | |
|---|---|---|---|---|---|---|
| 5,769,887 | A | 6/1998 | Brown et al. | 6,221,102 | B1 | 4/2001 | Baker et al. |
| 5,782,855 | A | 7/1998 | Lau et al. | 6,231,563 | B1 | 5/2001 | White et al. |
| 5,782,909 | A | 7/1998 | Quiachon et al. | 6,261,316 | B1 | 7/2001 | Shaolian et al. |
| 5,800,456 | A | 9/1998 | Maeda et al. | 6,264,682 | B1 | 7/2001 | Wilson et al. |
| 5,800,508 | A | 9/1998 | Goicoechea et al. | 6,273,909 | B1 | 8/2001 | Kugler et al. |
| 5,800,526 | A | 9/1998 | Anderson et al. | 6,280,466 | B1 | 8/2001 | Kugler et al. |
| 5,810,836 | A | 9/1998 | Hussein et al. | 6,280,467 | B1 | 8/2001 | Leonhardt |
| 5,824,037 | A | 10/1998 | Fogarty et al. | 6,283,991 | B1 | 9/2001 | Cox et al. |
| 5,824,039 | A | 10/1998 | Piplani et al. | 6,348,066 | B1 | 2/2002 | Pinchuk et al. |
| 5,824,040 | A | 10/1998 | Cox et al. | 6,350,278 | B1 | 2/2002 | Lenker et al. |
| 5,824,053 | A | 10/1998 | Khosravi et al. | 6,352,553 | B1 | 3/2002 | van der Burg et al. |
| 5,843,160 | A | 12/1998 | Rhodes | 6,352,561 | B1 | 3/2002 | Leopold et al. |
| 5,843,162 | A | 12/1998 | Inoue | 6,355,060 | B1 | 3/2002 | Lenker et al. |
| 5,843,164 | A | 12/1998 | Frantzen et al. | 6,361,544 | B1 | 3/2002 | Wilson et al. |
| 5,843,167 | A | 12/1998 | Dwyer et al. | 6,361,555 | B1 | 3/2002 | Wilson |
| 5,851,228 | A | 12/1998 | Pinheiro | 6,361,557 | B1 | 3/2002 | Gittings et al. |
| 5,855,599 | A | 1/1999 | Wan | 6,361,637 | B2 | 3/2002 | Martin et al. |
| 5,860,998 | A | 1/1999 | Robinson et al. | 6,383,213 | B2 | 5/2002 | Wilson et al. |
| 5,867,432 | A | 2/1999 | Toda | 6,387,120 | B2 | 5/2002 | Wilson et al. |
| 5,868,783 | A | 2/1999 | Tower | 6,395,017 | B1 | 5/2002 | Dwyer et al. |
| 5,871,536 | A | 2/1999 | Lazarus | 6,395,018 | B1 | 5/2002 | Castaneda |
| 5,879,321 | A | 3/1999 | Hill | 6,395,019 | B2 | 5/2002 | Chobotov |
| 5,879,366 | A | 3/1999 | Shaw et al. | 6,398,807 | B1 | 6/2002 | Chouinard et al. |
| 5,891,193 | A | 4/1999 | Robinson et al. | 6,409,750 | B1 | 6/2002 | Hyodoh et al. |
| 5,893,887 | A | 4/1999 | Jayaraman | 6,409,757 | B1 | 6/2002 | Trout, III et al. |
| 5,902,334 | A | 5/1999 | Dwyer et al. | 6,416,474 | B1 | 7/2002 | Penner et al. |
| 5,906,640 | A | 5/1999 | Penn et al. | 6,416,542 | B1 | 7/2002 | Marcade et al. |
| 5,906,641 | A | 5/1999 | Thompson et al. | 6,428,567 | B2 | 8/2002 | Wilson et al. |
| 5,916,263 | A | 6/1999 | Goicoechea et al. | 6,432,131 | B1 | 8/2002 | Ravenscroft |
| 5,919,225 | A | 7/1999 | Lau et al. | 6,432,134 | B1 | 8/2002 | Anson et al. |
| 5,925,075 | A | 7/1999 | Myers et al. | 6,440,161 | B1 | 8/2002 | Madrid et al. |
| 5,928,279 | A | 7/1999 | Shannon et al. | 6,464,721 | B1 | 10/2002 | Marcade et al. |
| 5,935,161 | A | 8/1999 | Robinson et al. | 6,475,166 | B1 | 11/2002 | Escano |
| 5,938,696 | A | 8/1999 | Goicoechea et al. | 6,475,170 | B1 | 11/2002 | Doron et al. |
| 5,948,018 | A | 9/1999 | Dereume et al. | 6,491,719 | B1 | 12/2002 | Fogarty et al. |
| 5,957,973 | A | 9/1999 | Quiachon et al. | 6,500,202 | B1 | 12/2002 | Shaolian et al. |
| 5,961,546 | A | 10/1999 | Robinson et al. | 6,508,833 | B2 | 1/2003 | Pavcnik et al. |
| 5,961,548 | A | 10/1999 | Shmulewitz | 6,508,835 | B1 | 1/2003 | Shaolian et al. |
| 6,001,125 | A | 12/1999 | Golds et al. | 6,508,836 | B2 | 1/2003 | Wilson et al. |
| 6,004,347 | A | 12/1999 | McNamara et al. | 6,511,325 | B1 | 1/2003 | Lalka et al. |
| 6,004,348 | A | 12/1999 | Banas et al. | 6,514,281 | B1 | 2/2003 | Blaeser et al. |
| 6,017,363 | A | 1/2000 | Hojeibane | 6,517,572 | B2 | 2/2003 | Kugler et al. |
| 6,027,779 | A | 2/2000 | Campbell et al. | 6,517,573 | B1 | 2/2003 | Pollock et al. |
| 6,027,811 | A | 2/2000 | Campbell et al. | 6,520,988 | B1 | 2/2003 | Colombo et al. |
| 6,030,415 | A | 2/2000 | Chuter | 6,524,335 | B1 | 2/2003 | Hartley et al. |
| 6,039,749 | A | 3/2000 | Marin et al. | 6,533,811 | B1 | 3/2003 | Ryan et al. |
| 6,039,755 | A | 3/2000 | Edwin et al. | 6,551,350 | B1 | 4/2003 | Thornton et al. |
| 6,039,758 | A | 3/2000 | Quiachon et al. | 6,558,396 | B1 | 5/2003 | Inoue |
| 6,045,557 | A | 4/2000 | White et al. | 6,562,063 | B1 | 5/2003 | Euteneuer et al. |
| 6,051,020 | A | 4/2000 | Goicoechea et al. | 6,565,596 | B1 | 5/2003 | White et al. |
| 6,053,940 | A | 4/2000 | Wijay | 6,565,597 | B1 | 5/2003 | Fearnot et al. |
| 6,063,113 | A | 5/2000 | Kavteladze et al. | RE38,146 | E | 6/2003 | Palmaz et al. |
| 6,070,589 | A | 6/2000 | Keith et al. | 6,572,645 | B2 | 6/2003 | Leonhardt |
| 6,074,398 | A | 6/2000 | Leschinsky | 6,576,009 | B2 | 6/2003 | Ryan et al. |
| 6,077,296 | A | 6/2000 | Shokoohi et al. | 6,579,312 | B2 | 6/2003 | Wilson et al. |
| 6,077,297 | A | 6/2000 | Robinson et al. | 6,582,390 | B1 | 6/2003 | Sanderson |
| 6,086,611 | A | 7/2000 | Duffy et al. | 6,582,460 | B1 | 6/2003 | Cryer |
| 6,090,128 | A | 7/2000 | Douglas | 6,585,758 | B1 | 7/2003 | Chouinard et al. |
| 6,093,203 | A | 7/2000 | Uflacker | 6,589,213 | B2 | 7/2003 | Reydel |
| 6,106,548 | A | 8/2000 | Roubin et al. | 6,592,614 | B2 | 7/2003 | Lenker et al. |
| 6,117,167 | A | 9/2000 | Goicoechea et al. | 6,592,615 | B1 | 7/2003 | Marcade et al. |
| 6,123,722 | A | 9/2000 | Fogarty et al. | 6,599,315 | B2 | 7/2003 | Wilson |
| 6,123,723 | A | 9/2000 | Konya et al. | 6,613,073 | B1 | 9/2003 | White et al. |
| 6,126,685 | A | 10/2000 | Lenker et al. | 6,616,675 | B1 | 9/2003 | Evard et al. |
| 6,129,756 | A | 10/2000 | Kugler et al. | 6,652,579 | B1 | 11/2003 | Cox et al. |
| 6,143,002 | A * | 11/2000 | Vietmeier .................... 606/108 | 6,669,718 | B2 | 12/2003 | Besselink |
| 6,146,415 | A * | 11/2000 | Fitz .............................. 623/1.11 | 6,689,157 | B2 | 2/2004 | Madrid et al. |
| 6,165,195 | A | 12/2000 | Wilson et al. | 6,733,523 | B2 | 5/2004 | Shaolian et al. |
| 6,168,610 | B1 | 1/2001 | Marin et al. | 6,761,733 | B2 | 7/2004 | Chobotov et al. |
| 6,171,281 | B1 | 1/2001 | Zhang | 6,767,359 | B2 | 7/2004 | Weadock |
| 6,183,481 | B1 | 2/2001 | Lee et al. | 6,800,065 | B2 | 10/2004 | Clarke et al. |
| 6,183,509 | B1 | 2/2001 | Dibie | 6,814,752 | B1 | 11/2004 | Chuter |
| 6,187,036 | B1 | 2/2001 | Shaolian et al. | 6,818,014 | B2 | 11/2004 | Brown et al. |
| 6,192,944 | B1 | 2/2001 | Greenhalgh | 6,821,292 | B2 | 11/2004 | Pazienza et al. |
| 6,197,049 | B1 | 3/2001 | Shaolian et al. | 6,827,726 | B2 | 12/2004 | Parodi |
| 6,203,735 | B1 | 3/2001 | Edwin et al. | 6,875,229 | B2 | 4/2005 | Wilson et al. |
| 6,210,429 | B1 | 4/2001 | Vardi et al. | 6,896,699 | B2 | 5/2005 | Wilson et al. |
| 6,221,090 | B1 | 4/2001 | Wilson | 6,899,728 | B1 | 5/2005 | Phillips et al. |
| 6,221,098 | B1 | 4/2001 | Wilson | 6,908,477 | B2 | 6/2005 | McGuckin |

| | | |
|---|---|---|
| 6,923,829 B2 | 8/2005 | Boyle et al. |
| 6,929,661 B2 | 8/2005 | Bolduc et al. |
| 6,932,837 B2 | 8/2005 | Amplatz et al. |
| 6,939,371 B2 | 9/2005 | Kugler et al. |
| 6,939,377 B2 | 9/2005 | Jayaraman et al. |
| 6,942,692 B2 | 9/2005 | Landau et al. |
| 6,942,693 B2 | 9/2005 | Chouinard et al. |
| 6,953,475 B2 | 10/2005 | Shaolian et al. |
| 6,955,688 B2 | 10/2005 | Wilson et al. |
| 6,960,217 B2 | 11/2005 | Bolduc |
| 6,962,602 B2 | 11/2005 | Vardi |
| 6,981,982 B2 | 1/2006 | Armstrong et al. |
| 6,984,244 B2 | 1/2006 | Perez et al. |
| 6,994,722 B2 | 2/2006 | DiCarlo |
| 7,004,964 B2 | 2/2006 | Thompson et al. |
| 7,004,967 B2 | 2/2006 | Chouinard et al. |
| 7,014,653 B2 | 3/2006 | Ouriel et al. |
| 7,025,779 B2 | 4/2006 | Elliott |
| 7,029,496 B2 | 4/2006 | Rakos et al. |
| 7,074,236 B2 | 7/2006 | Rabkin et al. |
| 7,122,051 B1 | 10/2006 | Dallara et al. |
| 7,122,052 B2 | 10/2006 | Greenhalgh |
| 7,125,464 B2 | 10/2006 | Chobotov et al. |
| 7,160,318 B2 | 1/2007 | Greenberg et al. |
| 7,163,715 B1 | 1/2007 | Kramer |
| 7,175,652 B2 | 2/2007 | Cook et al. |
| 7,175,657 B2 | 2/2007 | Khan et al. |
| 7,189,256 B2 | 3/2007 | Smith |
| 7,201,770 B2 | 4/2007 | Johnson et al. |
| 7,235,095 B2 | 6/2007 | Haverkost et al. |
| 7,244,444 B2 | 7/2007 | Bates |
| 7,261,733 B1 | 8/2007 | Brown et al. |
| 7,264,631 B2 | 9/2007 | DiCarlo |
| 7,264,632 B2 | 9/2007 | Wright et al. |
| 7,267,685 B2 | 9/2007 | Butaric et al. |
| 7,270,675 B2 | 9/2007 | Chun et al. |
| 7,314,483 B2 | 1/2008 | Landau et al. |
| 7,320,703 B2 | 1/2008 | DiMatteo et al. |
| 7,402,168 B2 | 7/2008 | Sanderson et al. |
| 7,425,219 B2 | 9/2008 | Quadri et al. |
| 7,491,230 B2 | 2/2009 | Holman et al. |
| 7,520,895 B2 | 4/2009 | Douglas et al. |
| 7,537,606 B2 | 5/2009 | Hartley |
| 7,553,324 B2 | 6/2009 | Andreas et al. |
| 7,572,289 B2 | 8/2009 | Sisken et al. |
| 7,637,932 B2 | 12/2009 | Bolduc et al. |
| 7,651,519 B2 | 1/2010 | Dittman |
| 7,674,284 B2 | 3/2010 | Melsheimer |
| 7,691,135 B2 | 4/2010 | Shaolian et al. |
| 7,722,657 B2 | 5/2010 | Hartley |
| 7,833,259 B2 | 11/2010 | Boatman |
| 2002/0049412 A1 | 4/2002 | Madrid et al. |
| 2002/0156516 A1 | 10/2002 | Vardi |
| 2003/0004560 A1 | 1/2003 | Chobotov et al. |
| 2003/0097169 A1 | 5/2003 | Brucker et al. |
| 2003/0176910 A1* | 9/2003 | Vrba et al. ............ 623/1.11 |
| 2004/0138735 A1 | 7/2004 | Shaolian et al. |
| 2004/0143312 A1* | 7/2004 | Samson et al. ............ 607/105 |
| 2004/0167618 A1 | 8/2004 | Shaolian et al. |
| 2004/0176832 A1 | 9/2004 | Hartley et al. |
| 2005/0038494 A1 | 2/2005 | Eidenschink |
| 2005/0058327 A1 | 3/2005 | Pieper |
| 2005/0059994 A1 | 3/2005 | Walak et al. |
| 2005/0060025 A1 | 3/2005 | Mackiewicz et al. |
| 2005/0113693 A1 | 5/2005 | Smith et al. |
| 2005/0113853 A1* | 5/2005 | Noriega et al. ............ 606/159 |
| 2005/0113905 A1 | 5/2005 | Greenberg et al. |
| 2005/0119731 A1 | 6/2005 | Brucker et al. |
| 2005/0121120 A1 | 6/2005 | Van Dijk et al. |
| 2005/0159803 A1 | 7/2005 | Lad et al. |
| 2005/0165480 A1 | 7/2005 | Jordan et al. |
| 2005/0171598 A1 | 8/2005 | Schaeffer |
| 2005/0240153 A1 | 10/2005 | Opie |
| 2005/0240258 A1 | 10/2005 | Bolduc et al. |
| 2005/0240260 A1 | 10/2005 | Bolduc |
| 2006/0074475 A1 | 4/2006 | Gumm |
| 2006/0100686 A1 | 5/2006 | Bolduc et al. |
| 2006/0178726 A1* | 8/2006 | Douglas ............ 623/1.16 |
| 2006/0233990 A1 | 10/2006 | Humphrey et al. |
| 2006/0233991 A1 | 10/2006 | Humphrey et al. |
| 2006/0259063 A1* | 11/2006 | Bates et al. ............ 606/198 |
| 2007/0027531 A1 | 2/2007 | DiMatteo et al. |
| 2007/0203571 A1 | 8/2007 | Kaplan et al. |
| 2007/0213804 A1 | 9/2007 | Kaplan et al. |
| 2007/0299499 A1 | 12/2007 | Hartley |
| 2008/0015681 A1 | 1/2008 | Wilson |
| 2008/0071343 A1 | 3/2008 | Mayberry et al. |
| 2008/0086191 A1 | 4/2008 | Valencia |
| 2008/0109065 A1 | 5/2008 | Bowe |
| 2009/0012602 A1 | 1/2009 | Quadri |
| 2009/0105806 A1 | 4/2009 | Benjamin et al. |
| 2010/0179636 A1 | 7/2010 | Mayberry et al. |
| 2010/0280588 A1 | 11/2010 | Schreck |
| 2011/0015718 A1 | 1/2011 | Schreck |
| 2011/0022153 A1 | 1/2011 | Schreck et al. |
| 2011/0054586 A1 | 3/2011 | Mayberry et al. |
| 2011/0054587 A1 | 3/2011 | Mayberry et al. |
| 2011/0054594 A1 | 3/2011 | Mayberry et al. |

FOREIGN PATENT DOCUMENTS

| | | |
|---|---|---|
| EP | 0 621 015 A1 | 10/1994 |
| EP | 0 659 389 A1 | 6/1995 |
| EP | 0 688 545 | 12/1995 |
| EP | 0 740 928 A2 | 11/1996 |
| EP | 0 775 470 A1 | 5/1997 |
| EP | 0 782 841 | 7/1997 |
| EP | 0 783 873 A2 | 7/1997 |
| EP | 0 783 874 A2 | 7/1997 |
| EP | 0 904 745 A2 | 3/1999 |
| EP | 0 732 088 B1 | 4/2000 |
| EP | 1 433 438 | 6/2004 |
| ES | 1 038 606 | 7/1998 |
| JP | 04-25755 | 1/1992 |
| WO | WO 94/24961 | 11/1994 |
| WO | WO 96/34580 | 11/1996 |
| WO | WO 97/26936 | 1/1997 |
| WO | WO 97/10757 | 3/1997 |
| WO | WO 97/45072 | 12/1997 |
| WO | WO 99/44536 | 9/1999 |
| WO | WO 99/47077 | 9/1999 |
| WO | WO 00/53251 A | 9/2000 |
| WO | WO 02/39888 A | 5/2002 |
| WO | WO 2005/037076 | 4/2005 |
| WO | WO 2005/037076 A2 | 4/2005 |
| WO | WO 2005/037141 A | 4/2005 |
| WO | WO 2005/037141 A | 4/2005 |

OTHER PUBLICATIONS

Patent Cooperation Treaty International Search Report for International application No. PCT/US2008/050915 filed on Nov. 1, 2008, 7 pages.

Patent Cooperation Treaty (PCT) International Search Report, International Application No. PCT/US2007/078565, Filed on Sep. 14, 2007, in 7 pages.

U.S. Appl. No. 12/101,863, filed Apr. 11, 2008, amd its ongoing prosecution history, including without limitation Office Actions, Amendments, Remarks, and any other potentially relevant documents, Mayberry et al.

The International Bureau of WIPO, "International Preliminary Report on Patentability (Chapter 1 of the Patent Cooperation Treaty" and "Written Opinion of the International Searching Authority" of PCT application PCT/US2008/050915, date of issuance: Jul. 14, 2009, in 10 pages.

U.S. Appl. No. 12/390,346, filed Feb. 20, 2009, and its ongoing prosecution history, including without limitation Office Actions, Amendments, Remarks, and any other potentially relevant documents, Filing Date Feb. 20, 2009, Schreck et al.

U.S. Appl. No. 12/496,446, filed Jul. 1, 2009, and it's ongoing prosecution history, including without limitation Office Actions, Amendments, Remarks, and any other potentially relevan documents, Filing Date Jul. 1, 2009, Benjamin, et al.

US 5,690,647, 11/1997, Osborne (withdrawn)
US 6,413,270, 07/2002, Thornton et al. (withdrawn)

* cited by examiner

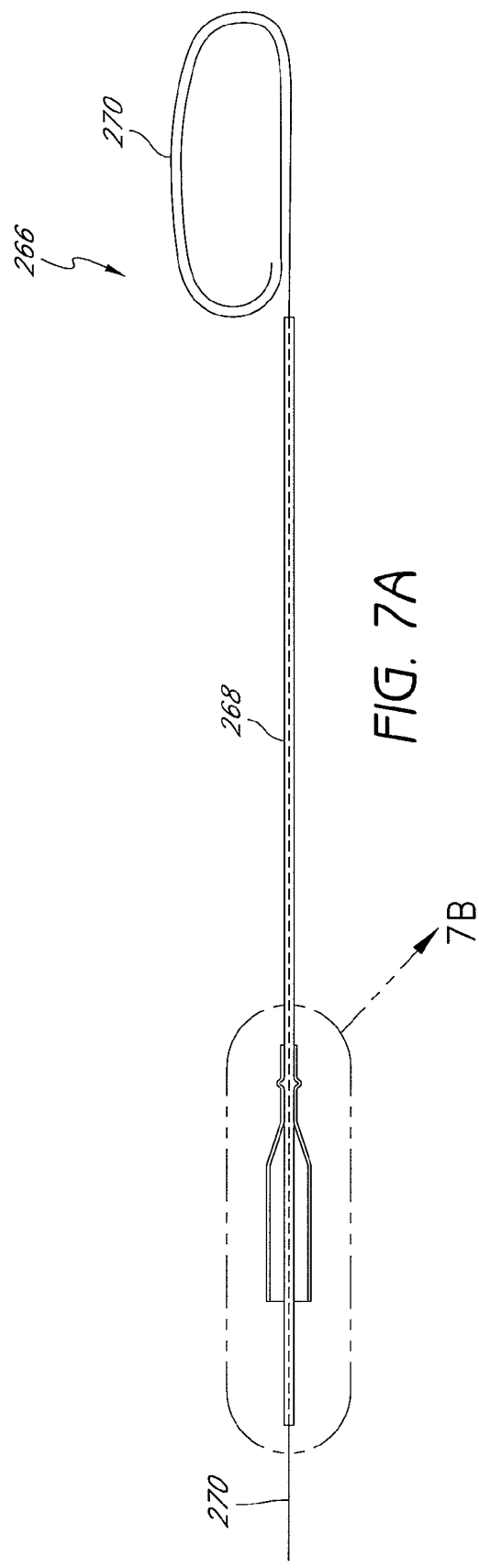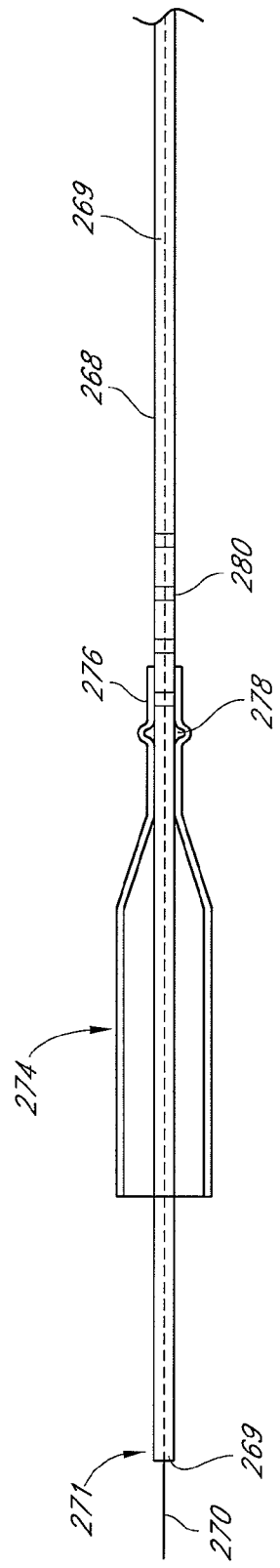

DUAL CONCENTRIC GUIDEWIRE AND METHODS OF BIFURCATED GRAFT DEPLOYMENT

BACKGROUND OF THE INVENTION

1. Field of the Invention

The present invention relates to endoluminal vascular prosthesis deployment, and in particular, to a dual concentric guidewire system for maintaining post deployment access to the treatment site.

2. Description of the Related Art

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of Polyester, Urethane, DACRON™, TEFLON™, or other suitable material.

To perform the surgical procedure requires exposure of the aorta through an abdominal incision which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON™ tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. The graft must be secured, or sutured, to the remaining portion of the aorta, which may be difficult to perform because of the thrombosis present on the remaining portion of the aorta. Moreover, the remaining portion of the aorta wall is frequently friable, or easily crumbled.

Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft within the lumen of the artery.

Endoluminal repair or exclusion of aortic aneurysms has been performed for the past several years. The goal of endoluminal aortic aneurysm exclusion has been to correct this life threatening disease in a minimally invasive manner in order to effectuate a patient's quick and complete recovery. Various vascular grafts exist in the prior art that have been used to exclude aortic aneurysms. In general, transluminally implantable prostheses adapted for use in the abdominal aorta comprise a tubular wire cage surrounded by a tubular PTFE or Dacron sleeve. Both balloon expandable and self expandable support structures have been proposed. Endovascular grafts adapted to treat both straight segment and bifurcation aneurysms have also been designed.

Endoluminal implantation is an increasingly accepted technique for implanting vascular grafts. Typically, this procedure involves percutaneously inserting a vascular graft or prosthesis by using a delivery catheter. This process eliminates the need for major surgical intervention thereby decreasing the risks associated with vascular and arterial surgery. Various catheter delivery systems for prosthetic devices are described in the prior art.

For example, certain current delivery systems for a bifurcated stent graft system or a graft having at least one branch portion use two sheaths moving in opposing directions to deploy the distal segment of the graft before the proximal segment. The outer sheath is first retracted to deploy a portion of the mid-body and the contralateral limb. Then, the front sheath is advanced distally to deploy the distal end of the graft. See e.g., U.S. Pat. No. 6,660,030. Other delivery systems, for example as disclosed in co-pending application Ser. No. 11/522,292, filed Sep. 15, 2006 and incorporated by reference herein in its entirety, may use a plurality of axially spaced releasable restraint members temporarily connected by a pull wire to allow the distal main graft portion to be deployed before a proximal graft portion. Typically, these delivery systems are delivered to the aneurysm location over a guidewire. The guidewire may be further used to release a branch graft portion of the prosthesis, for example, by operably connecting a branch graft restraint mechanism to the guidewire and proximally withdrawing the guidewire from the vasculature.

Once the bifurcation graft has been deployed and implanted, a variety of procedures may desirably be accomplished. For example, it may be advantageous to implant a cuff on the proximal end of the main graft portion to secure the graft and thereby prevent movement or slippage of the main graft portion. Alternatively, it may be necessary to dilate the stenosis or touch up or re-establish the expansion of the graft. These procedures require advancing another catheter to the graft location along a guidewire. However, the positioning of a guidewire through the graft after the graft has been deployed is difficult since the tip of the guidewire will snag on the wire support cage of the graft. Thus, it would be advantageous to provide a guidewire assembly configured to remain placed through a graft once the graft has been deployed and to allow access through the expanded graft for subsequent catheterizations.

SUMMARY OF THE INVENTION

Accordingly, one embodiment of the present invention comprises a self-expandable endoluminal vascular prosthesis deployment system that includes a deployment catheter for deploying an endoluminal vascular prosthesis having at least a main graft portion and a first branch graft portion. The deployment catheter has distal and proximal ends and a lumen extending therethrough. A hollow guidewire is slidably positioned within the deployment catheter. The hollow guidewire is coupled with a branch graft restraint member configured to releasably constrain the first branch graft portion. An inner core member is slidably positionable within said hollow guidewire. The inner core member has a length such that the proximal and distal ends of said inner core member extend beyond the proximal and distal ends of the hollow guide wire.

Another embodiment of the present invention comprises a method of deploying an endoluminal vascular prosthesis in a patient's artery. The method comprises positioning a hollow guidewire sheath across a bifurcation in a patient's artery and in a contralateral branch of said patient's artery. The hollow guidewire sheath has distal and proximal ends and a lumen extending therethrough. The distal end of said hollow guidewire sheath is slidably inserted into a deployment catheter. The proximal end of said hollow guidewire assembly extending from said contralateral branch outside said patient. The deployment catheter is advanced over through an iliac branch of said patient's artery. Traction is applied to the proximal end of the hollow guidewire sheath to remove slack from said hollow guidewire sheath. The deployment catheter is positioned at said bifurcation in the patient's artery. A main graft segment is deployed from the deployment catheter. The inner core wire is advanced distally through said lumen of said hollow guidewire sheath such that the inner core wire extends beyond the distal end of said hollow guidewire sheath and beyond the distal end of said main graft segment. The hollow guidewire sheath is retracted proximally. The hollow guidewire sheath is withdrawn from said patient's artery. The deployment catheter is withdrawn from the patient.

BRIEF DESCRIPTION OF THE DRAWINGS

FIG. 7A is a schematic representation of an embodiment of a dual concentric guidewire assembly of the present invention.

FIG. 7B is an enlarged detail view of the restraint member located on the guidewire assembly taken along the line 7B in FIG. 7A.

DETAILED DESCRIPTION OF THE PREFERRED EMBODIMENTS

Described below are various embodiments of a delivery system for deploying a vascular graft including a deployment catheter and a hollow guidewire assembly which may be used to maintain access through an implanted vascular graft for subsequent catheterizations. As used herein, the relative terms "proximal" and "distal" shall be defined from the perspective of the delivery system. Thus, proximal refers to the direction of the control end of the delivery system and distal refers to the direction of the distal tip. In certain embodiments, the deployment catheter is configured to deliver a graft that includes a main or distal graft portion and at least one branch or proximal graft portion. In certain embodiments, the hollow guidewire assembly may be associated with a restraint member for the branch segment, such that the branch segment may be deployed by the guidewire assembly. The guidewire assembly may be further configured such that it may be used to remove the restraint member from the branch segment while permitting placement and maintenance of a guidewire through the expanded branch segment and main body graft for subsequent catheterizations. Other embodiments of a graft deployment system and guidewire assembly will also be described below.

Figure 1:
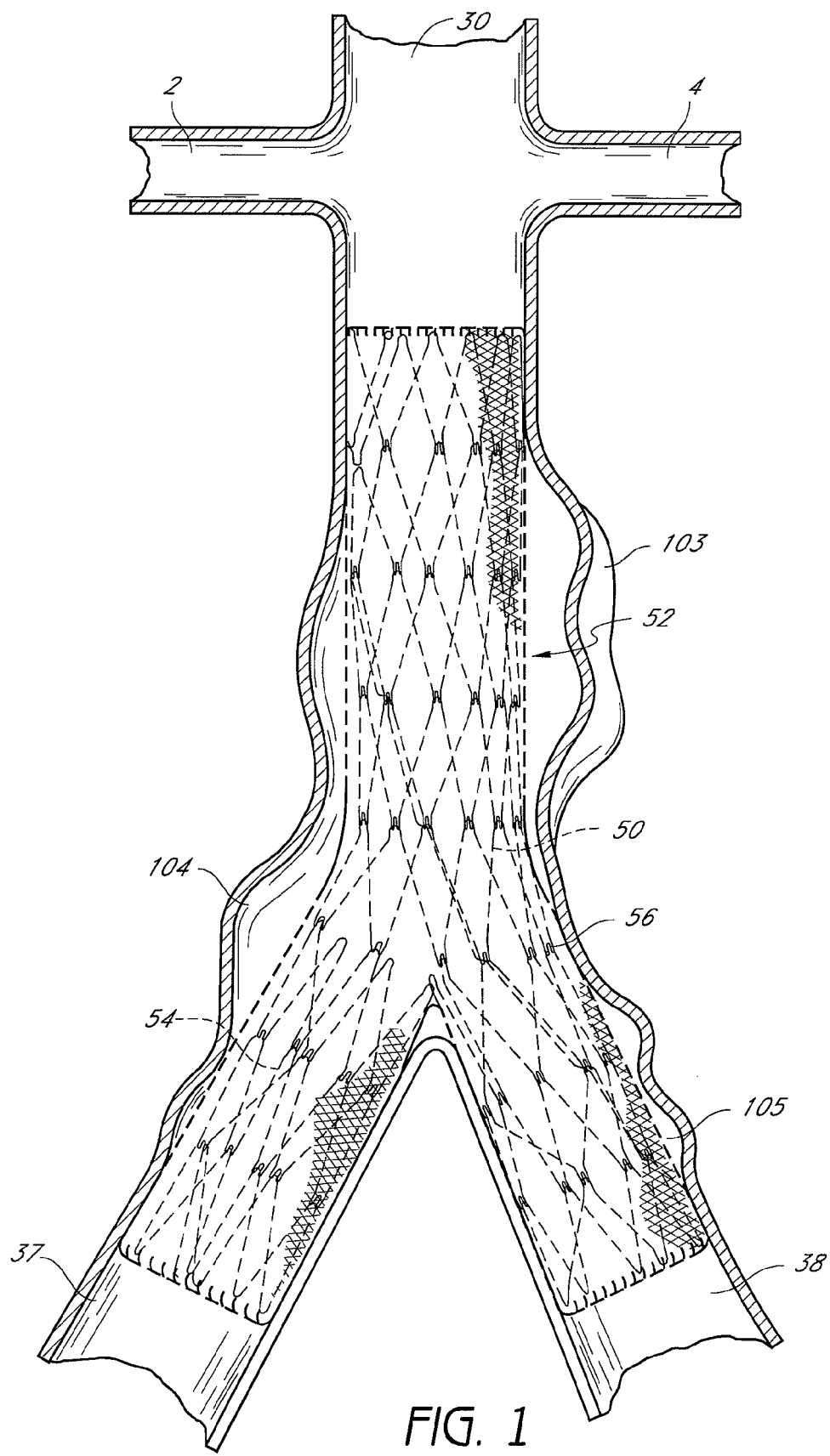
FIG. 1 is a schematic representation of a bifurcated vascular prosthesis for use with the present invention, positioned at the bifurcation between the abdominal aorta and the right and left common iliac arteries.

With reference to FIG. 1, there is illustrated a schematic representation of the abdominal part of the aorta and its principal branches. In particular, the abdominal aorta 30 is characterized by a right renal artery 2 and left renal artery 4. The large terminal branches of the aorta 30 are the right and left common iliac arteries 37 and 38. Additional vessels (e.g., second lumbar, testicular, inferior mesenteric, middle sacral) have been omitted from FIG. 1 for simplification. One embodiment of an expanded bifurcated endoluminal vascular prosthesis is shown spanning aneurysms 103, 104 and 105. The expanded bifurcated endoluminal vascular prosthesis 50 can comprise a main branch portion 52 for traversing the aorta, a first branch portion 54 for spanning an ipsilateral iliac and a second branch portion 56 for spanning a contralateral iliac.

Figure 2:
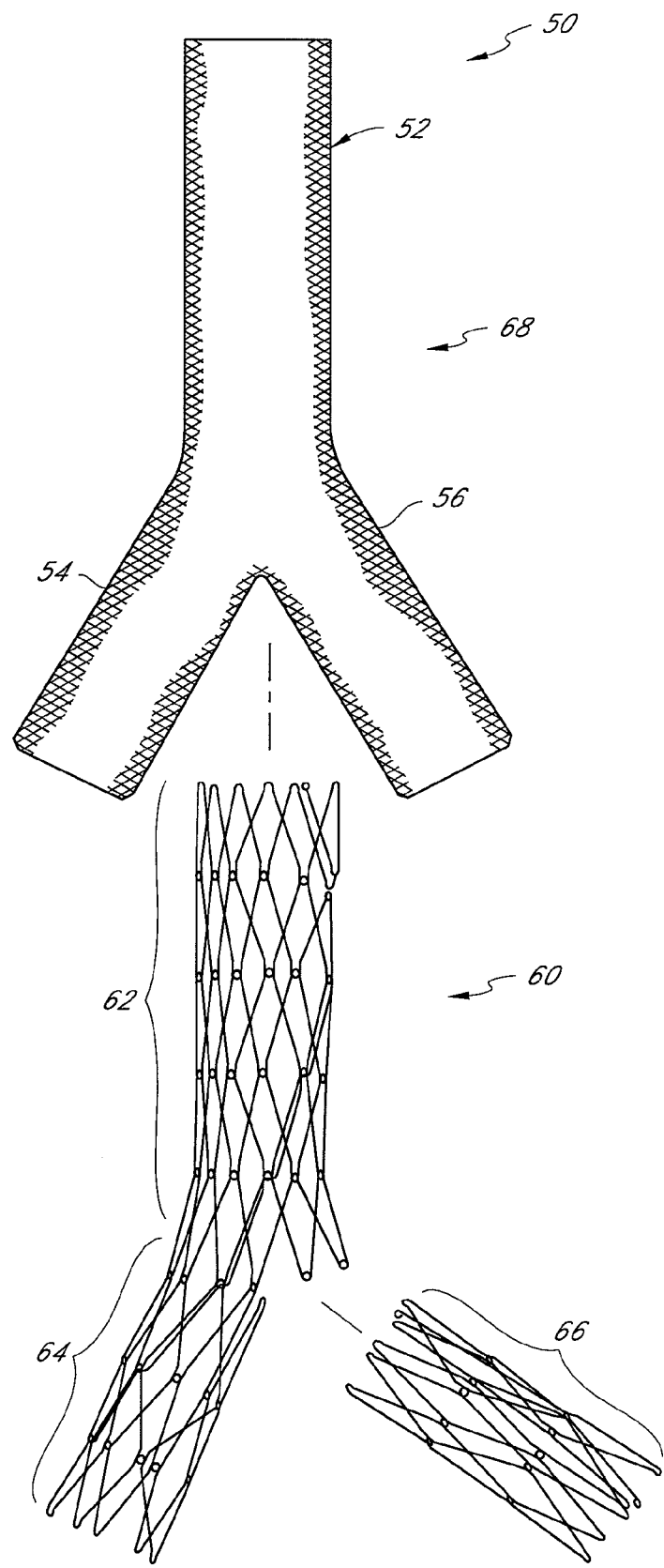
FIG. 2 is an exploded view of a bifurcated graft for use with the present invention, showing a self-expanding wire support cage separated from an outer polymeric sleeve.

As depicted in FIG. 2, the bifurcated prosthesis 50 can comprise a polymeric sleeve 68 and a tubular wire support 60. In the illustrated embodiment, the polymeric sleeve 60 can be situated concentrically outside of the tubular wire support 60. However, other embodiments may include a sleeve situated instead concentrically inside the wire support or on both of the inside and the outside of the wire support. Alternatively, the wire support may be embedded within a polymeric matrix or layer which makes up the sleeve. The sleeve 68 may be attached to the wire support 60 by any of a variety of suitable manners known to those skilled in the art.

The tubular wire support 60 can comprise a main branch portion 62 for traversing the aorta, a first branch portion 64 for spanning an ipsilateral iliac and a second branch portion 66 for spanning a contralateral iliac. The main branch portion 62 and first ipsilateral branch portion 64 can be formed from a continuous single length of wire having a proximal end, a distal end and a central lumen extending therebetween. Alternatively, the first ipsilateral branch portion 64 may be formed of one or more lengths of wire pivotably connected to the proximal end of the main branch portion 62. A second, contralateral branch component 66 may be formed of one or more lengths of wire pivotably connected to the proximal end of the main branch portion 62. Each of the iliac branch components has a proximal end, a distal end and a central lumen extending therethrough. Construction of the graft from a three part cage conveniently facilitates the use of different gauge wire in the different components (e.g. 0.014" diameter main trunk and 0.012" diameter branch components).

In general, each of the components of the bifurcated endoluminal vascular prosthesis 50 may be varied considerably in diameter, length, and expansion coefficient, depending upon the intended application. For implantation within the aorta of a typical adult, the main branch portion 52 will have a length within the range of from about 5 cm to about 12 cm, and, typically within the range of from about 9 cm to about 10 cm. The unconstrained outside expanded diameter of the main branch portion 52 will typically be within the range of from about 20 mm to about 40 mm. The unconstrained expanded outside diameter of the main branch portion 52 can be constant or substantially constant throughout the length, or can be tapered from a relatively larger diameter at the distal end to a relatively smaller diameter at the bifurcation. In general, the diameter of the proximal end of the main branch portion will be on the order of no more than about 95% and, preferably, no more than about 85% of the diameter of the distal end of the main branch portion. The iliac branch portions 54 and 56 will typically be bilaterally symmetrical, having a length within the range of from about 1 cm to about 6.5 cm, and a diameter within the range of from about 10 mm to about 20 mm.

The collapsed prosthesis for use in accordance with the present invention has a diameter in the range of about 2 mm to about 10 mm. Preferably, the maximum diameter of the collapsed prosthesis is in the range of about 3 mm to 6 mm (12 to 18 French). Some embodiments of the deployment catheter including the prosthesis will be in the range of from 18 to 20 or 21 French; other embodiments will be as low as 19 F, 16 F, 14 F, or smaller. After deployment, the expanded endoluminal vascular prosthesis may radially self-expand to a diameter anywhere in the range of about 20 to 40 mm.

Although certain prosthesis configurations are disclosed herein, these are only examples of prostheses which are deployable using the embodiments of a deployment catheter and guidewire assembly described herein. In other embodiments, the delivery system described below may be used to deliver and deploy other types of self expandable bifurcated or multi-segmented prosthesis having a main graft portion and at least one branch graft portion, as will be apparent to those of skill in the art in view of the disclosure herein. For example, in other embodiments, certain features and aspects of the deployment catheter and guidewire assembly can be used to deploy a graft without a branch graft portion, a graft with only one branch portion and/or a graft with more than one graft portions. Further details and additional embodiments of the prosthesis described above can be found in U.S. Pat. Nos. 6,007,296, 6,187,036, and 6,197,049, the entirety of which are hereby incorporated by reference herein.

It should also be appreciated that, although the illustrated embodiments are described in the context of a bifurcated graft configured for the abdominal aorta, certain features and aspects of the delivery systems and methods described herein can be used in other portions of the vascular system. For example, it is anticipated that certain features and aspects of the systems and methods described herein can be adapted for use in the thoracic aorta. It is also anticipated that certain features and aspects of the system described herein may be adapted to deliver a single straight graft segment to the thoracic aorta.

The self expandable bifurcation graft can be deployed at a treatment site with any of a variety of deployment catheters as will be apparent to those of skill in the art. Further details and additional embodiments of the deployment catheters suitable for deploying a self-expanding bifurcation graft can be found, for example in U.S. Pat. Nos. 6,500,202 and 6,090,128 and in U.S. patent application Ser. No. 11/522,292, filed Sep. 15, 2006, the entirety of these patents and patents applications hereby incorporated by reference herein.

Figure 3:
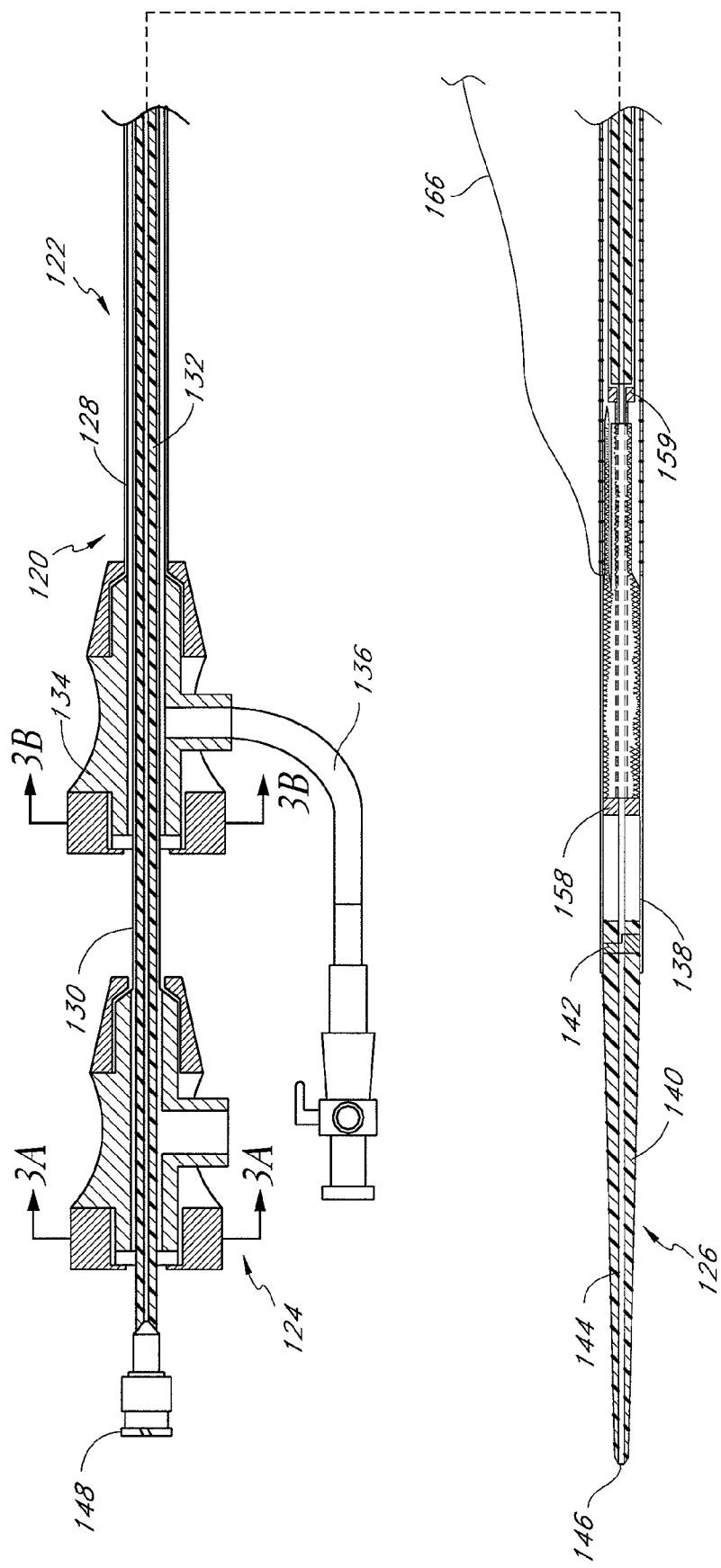
FIG. 3 is a cross-sectional view of an embodiment of a deployment catheter for delivering a bifurcated graft

For example, FIG. 3 is a cross-sectional side view of one embodiment of a deployment catheter 120 for deploying a bifurcated vascular prosthesis, such as the prosthesis 50 described above. The deployment catheter 120 comprises an elongate flexible multicomponent tubular body 122 having a proximal end 124 and a distal end 126. The tubular body 122 and other components of this system can be manufactured in accordance with any of a variety of techniques well known in the catheter manufacturing field. Suitable materials and dimensions can be readily selected taking into account the natural anatomical dimensions in the iliacs and aorta, together with the dimensions of the desired percutaneous access site.

The elongate flexible tubular body 122 comprises an outer sheath 128 which is axially movably positioned upon an intermediate tube 130. A central tubular core 132 is axially movably positioned within the intermediate tube 130. In one embodiment, the outer tubular sheath comprises extruded PTFE, having an outside diameter of about 0.250" and an inside diameter of about 0.230". The tubular sheath 128 is provided at its proximal end with a manifold 134, having a hemostatic valve 136 thereon and access ports such as for the infusion of drugs or contrast media as will be understood by those of skill in the art.

The outer tubular sheath 128 has an axial length within the range of from about 40 cm to about 55 cm. In one embodiment of the deployment catheter 120, having an overall length of 110 cm, the axial length of the outer tubular sheath 128 is about 52 cm and the outside diameter is no more than about 0.250". Thus, the distal end 129 of the tubular sheath 128 may be located at least about 16 cm proximally of the distal end 126 of the deployment catheter 120 in a stent loaded configuration.

A distal segment of the deployment catheter 120 comprises an outer tubular housing or cap 138, which terminates distally in an elongate flexible tapered distal tip 140. The distal housing 138 and tip 140 are axially immovably connected to the central core 132 at a connection 142.

In a preferred embodiment of the present invention, the central tubular core 132 is axially movably positioned within but rotationally locked to the intermediate tube 130. The intermediate tube 130 is preferably also axially movably positioned within but rotationally locked to the outer sheath 128. In this manner, the rotational orientation of the central tubular core 132 remains fixed with respect to the rotational orientation of the outer sheath 128.

Rotational engagement can be accomplished in any of a variety of ways, normally involving complementary surface structures such as keys or splines on the associated components. For example, the central tubular core 132 can be provided with a radially outwardly extending projection, along a portion or all of its axial length. This projection is slidably received within a radially outwardly extending slot on the interior surface of the intermediate tube 130, or component secured thereto. Alternatively, a radially inwardly extending projection on intermediate tube 130 or associated component can be received with an axially extending recess on the outer surface of the central tubular core 132. Alternatively, any of a variety of non-round configurations for the central tubular core 132 such as elliptical, oval, triangular, square, polygonal, and the like, can be slidably received within a complementary-shaped aperture on or connected to the intermediate tube 130.

Figure 3B:
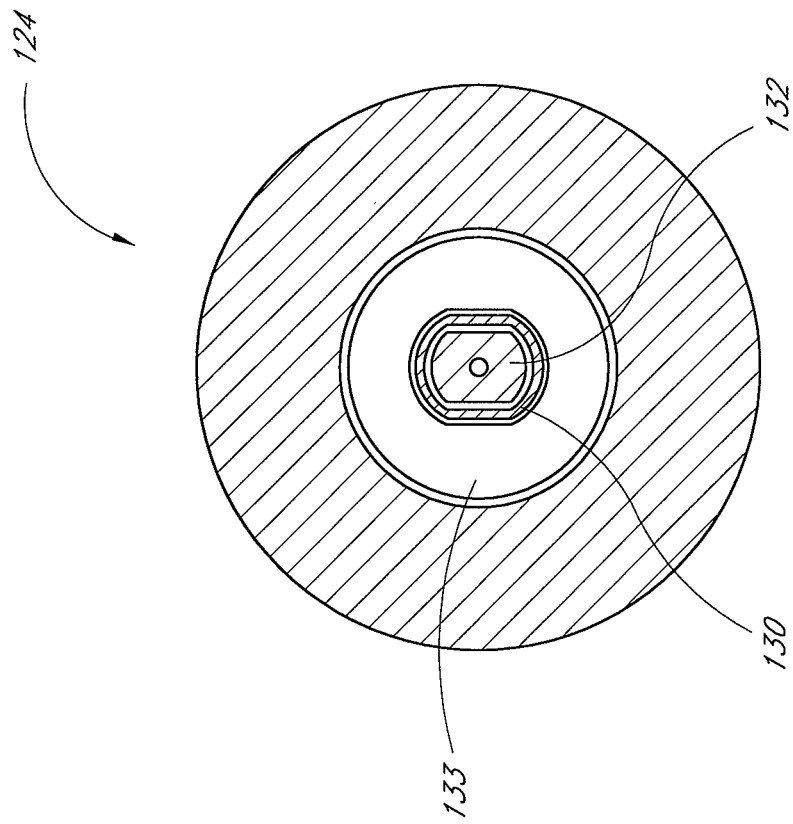
FIG. 3B is a cross-section taken along line 3B-3B of FIG. 3.
Figure 3A:
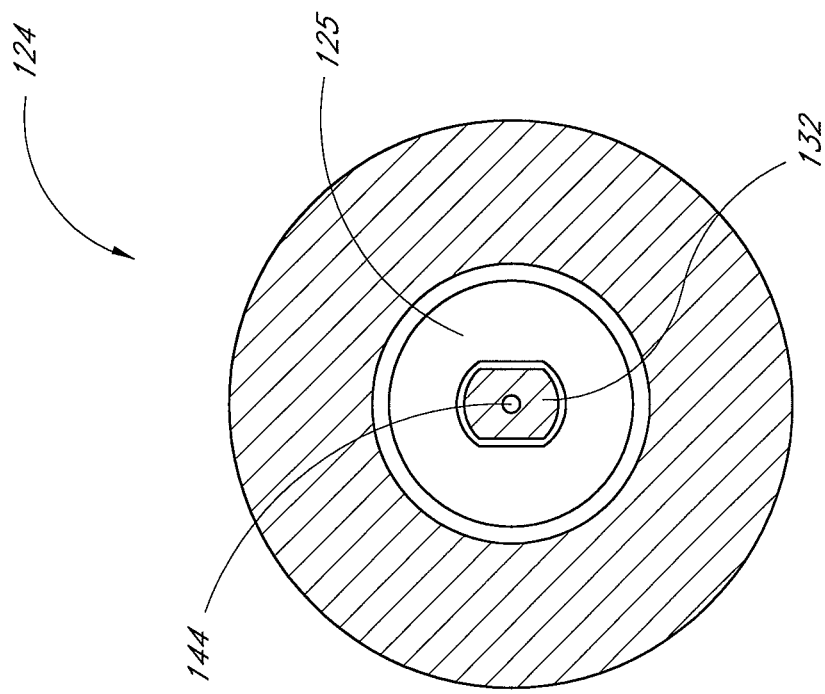
FIG. 3A is a cross-section taken along line 3A-3A of FIG. 3.

In the illustrated embodiment, as shown in FIGS. 3A-3B, the cross section of the central tubular core 132 deviates from circular by the provision of one or two opposing flat sides extending axially along its length. A corresponding aperture is provided in a rotational lock 125 provided at the proximal end of the intermediate tube 130. Thus, rotation of the intermediate tube 130 will cause a similar rotation of the central tubular core 132.

Similarly, as shown in FIG. 3B, the intermediate tube 130 is provided with one or two opposing flat surfaces to be slidably received through a complementary aperture in a rotational lock 133 on manifold 134. The resulting assembly enables rotation of the manifold 134 to cause a commensurate rotation of the intermediate tube 130 and central tubular core 132. Specific dimensions and design details of the rotational lock disclosed herein will be readily apparent to those of skill in the art in view of the disclosure herein.

Figure 4:
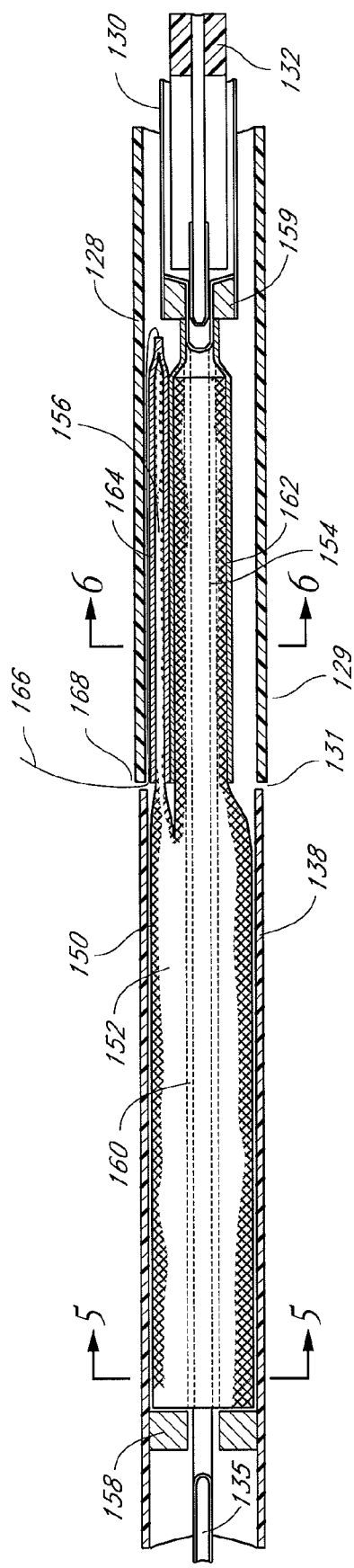
FIG. 4 is an enlargement of the portion delineated by the line 4-4 in FIG. 4.

As can be seen from FIG. 4, a junction 131 is formed between the distal end 129 of outer sheath 128 and outer tubular housing 138. Proximal retraction of the outer sheath 128 with respect to the intermediate tube 130 and outer tubular housing 138 will expose the compressed iliac branches of the graft, as will be discussed in more detail below.

The distal tip 140 (see FIG. 3) preferably tapers from an outside diameter of about 0.225" at its proximal end to an outside diameter of about 0.070" at the distal end thereof. The overall length of the distal tip 140 in one embodiment of the deployment catheter 120 is about 3". However, the length and rate of taper of the distal tip 140 can be varied depending upon the desired trackability and flexibility characteristics. The distal end of the housing 138 is secured to the proximal end of the distal tip 140 such as by thermal bonding, adhesive bonding, and/or any of a variety of other securing techniques known in the art. The proximal end of distal tip 140 is preferably also directly or indirectly connected to the central core 132 such as by a friction fit and/or adhesive bonding.

In at least the distal section of the catheter, the central core 132 preferably comprises a length of hypodermic needle tubing 135. The hypodermic needle 135 tubing may extend throughout the length of the catheter to the proximal end thereof, or may be secured to the distal end of a proximal extrusion as illustrated for example in FIG. 6. A central guidewire lumen 144 extends throughout the length of the tubular central core 132, having a distal exit port 146 and a proximal access port 148 as will be understood by those of skill in the art. In use, the deployment catheter will be advanced into position in the aorta over a guidewire extending through the central guidewire lumen as will be understood by those of skill in the art.

Figure 6:
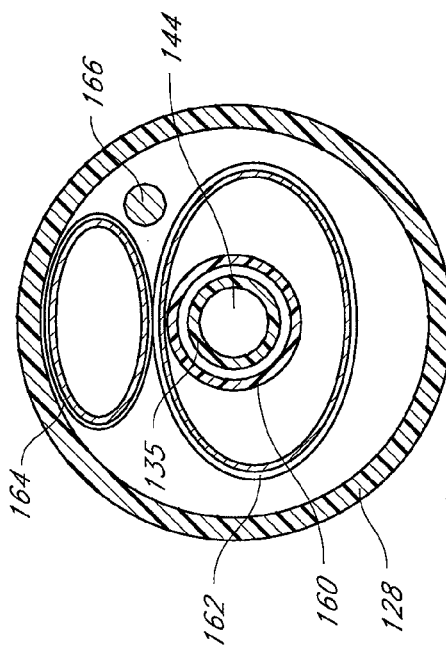
FIG. 6 is a cross-section taken along the line 6-6 in FIG. 4.
Figure 5:
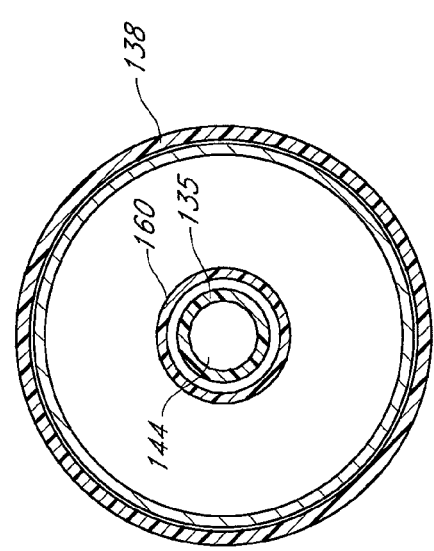
FIG. 5 is a cross-section taken along the line 5-5 in FIG. 4.

Referring to FIGS. 4-6, a bifurcated endoluminal graft 150 is illustrated in a compressed configuration within the deployment catheter 120. The graft 150 comprises a distal aortic trunk portion 152, a proximal ipsilateral iliac portion 154, and a proximal contralateral iliac portion 156. The aortic trunk 152 of the graft 150 is contained within the tubular housing 138. Distal axial advancement of the central tubular core 132 will cause the distal tip 140 and housing 138 to advance distally with respect to the graft 150, thereby permitting the aortic trunk portion 152 of the graft 150 to expand to its larger, unconstrained diameter. Distal travel of the graft 150 is prevented by a distal stop 158 which is axially immovably connected to the intermediate tube 130. Distal stop 158 may comprise any of a variety of structures, such as an annular flange or component which is adhered to, bonded to or integrally formed with a tubular extension 160 of the intermediate tube 130. Tubular extension 160 is axially movably positioned over the hypotube central core 132.

The tubular extension 160 extends axially throughout the length of the graft 150. At the proximal end of the graft 150, a step 159 axially immovably connects the tubular extension 160 to the intermediate tube 130. In addition, the step 159 provides a proximal stop surface to prevent proximal travel of the graft 150 on the catheter 120. The function of step 159 can be accomplished through any of a variety of structures as will be apparent to those of skill in the art in view of the disclosure herein. For example, the step 159 may comprise an annular ring or spacer which receives the tubular extension 160 at a central aperture therethrough, and fits within the distal end of the intermediate tube 130. Alternatively, the intermediate tube 130 can be reduced in diameter through a generally conical section or shoulder to the diameter of tubular extension 160.

Proximal retraction of the outer sheath 128 will release the compressed iliac branches 154 and 156 of the graft 150. The iliac branches 154 and 156 will remain compressed, within a first (ipsilateral) tubular sheath 162 and a second (contralateral) tubular sheath 164. The first tubular sheath 162 is configured to restrain the ipsilateral branch of the graft 150 in the constrained configuration, for implantation at the treatment site. The first tubular sheath 162 is connected to the intermediate core 130 and is adapted to be axially proximally withdrawn from the iliac branch, thereby permitting the branch graft portion to expand to its implanted configuration. In one embodiment, the first tubular sheath 162 comprises a thin walled PTFE extrusion having an outside diameter of about 0.215" and an axial length of about 7.5 cm. A proximal end of the tubular sheath 162 is necked down such as by heat shrinking to secure the first tubular sheath 162 to the tubular extension 160. In this manner, proximal withdrawal of the intermediate tube 130 will in turn proximally retract the first tubular sheath 162 relative to the graft 150, thereby deploying the self expandable ipsilateral iliac branch of the graft 150.

The second tubular sheath 164 is connected to a contralateral guidewire 166 which extends outside of the tubular body 122 at a point 168, such as may be conveniently provided at the junction 131 between the outer tubular sheath 128 and the distal housing 138. The second tubular sheath 164 is adapted to restrain the contralateral branch of the graft 156 in the reduced profile. In one embodiment of the invention, the second tubular sheath 164 has an outside diameter of about 0.215" and an axial length of about 7.5 cm. The second tubular sheath 164 can have a significantly smaller cross-section than the first tubular sheath 162, due to the presence of a smaller tubular core 132 and intermediate tube 130 within the first iliac branch 154. Proximal retraction of the contralateral guidewire through the contralateral iliac will proximally withdraw the second tubular sheath 164 from the contralateral graft portion 156 and thereby deploy the contralateral graft portion 156.

In one embodiment, the contralateral guidewire 166 may comprise a dual concentric guidewire assembly 266 including a hollow guidewire sheath and an inner core wire. Referring to FIGS. 7A-B, the dual concentric guidewire assembly 266 includes a hollow guidewire sheath 268 and an inner core wire 270 configured to be axially advanced through a lumen 269 in the hollow guidewire sheath 268. In one embodiment, the length of the hollow guidewire sheath 268 may be between about 80 cm and about 140 cm, or alternatively between about 90 cm and about 140 cm, or in one embodiment approximately 136 cm. In general, the axial length of the hollow guidewire sheath 268 should be sufficient to extend from a point outside of the body through an ipsilateral iliac puncture across the bifurcation between the contralateral and ipsilateral iliacs to a second point outside the body through a contralateral access site. Thus, the length can vary depending upon the intended access site location along the femoral artery and the desired length of the guidewire sheath 268 which is to extend outside of the body.

The hollow guidewire sheath 268 may be formed in any of a variety of manners which are well known in the art of catheter body manufacturing, such as by braiding and/or extrusion. Suitable extrudable materials include high density polyethylene, medium density polyethylene and other polyethylene blends, nylon, PEBAX, and others well known in the art. Reinforced tubular bodies may be produced by including a braided layer in or on the wall. The braided wall may comprise any of a variety of materials such as stainless steel, nitinol, composite fibers and others known in the art.

In one embodiment, the hollow guidewire sheath 268 comprises a PEBAX extrusion, having a braided wire for reinforcing the lumen. The braid filament comprises a round wire having a cross section of about 0.002 inches. Alternatively, the hollow guidewire sheath 268 may comprise a stainless steel coil covered by a polyimide tubing that is again covered by PTFE heatshrink. The outer diameter of the hollow guidewire sheath is between about 0.025-0.045 inches, alternatively between about 0.020-0.040 inches, alternatively about 0.035 inches. The hollow guidewire sheath 268 includes a central lumen 269 extending from the distal end to the proximal end such that the inner core wire 270 may be axially advanced through the central lumen 269. The central lumen 269 has an inner diameter of between about 0.020-0.016 inches, alternatively between about 0.019-0.017 inches, in one implementation about 0.018 inches such that an inner core wire 270, having a diameter of no more than about 0.016 inches, can be axially advanced therethrough.

The inner core wire 270 may, in certain embodiments, comprise a 0.014 inch guidewire. In alternative embodiments, the inner core wire 270 can comprise any of a variety of structures, including polymeric monofilament materials, braided or woven materials, metal ribbon or wire, or conventional guidewires as are well known in the art. The inner core wire may have a length of between about 180-360 cm, alternatively between about 200-340 cm, alternatively between about 220-300 cm. For example in certain embodiments, the inner core wire may be approximately 190 cm, 240 cm, or alternatively 300 cm. In general, the length of the inner core wire should be between 1.5 to three times the length of the hollow guidewire sheath, and is often about twice the length of the hollow guidewire sheath, such that in use, positive contact may be maintained with the inner wire while the hollow guidewire sheath is being withdrawn from a patient over the inner core wire. Positive contact with the inner core wire will prevent friction between the inner core wire and the hollow guidewire sheath from withdrawing the inner core wire as well as the hollow guidewire.

Figure 8:
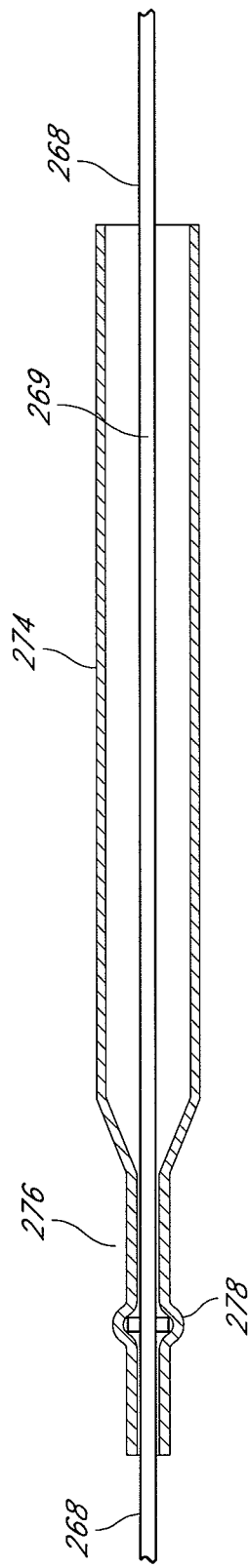
FIG. 8 is a schematic representation of an embodiment of the distal end of a dual concentric guidewire assembly.

In certain embodiments, a branch graft restraint mechanism 274, may be coupled to the hollow guidewire sheath 268 such that in use proximal retraction of the hollow guidewire sheath 268 releases a self-expanding branch graft portion from the branch graft restraint mechanism 274. For example, in one embodiment, as depicted in FIGS. 7A-B and 8, a branch graft restraint mechanism 274 comprising an open-ended tubular sheath, such as a tubular sheath described above, is mounted on the outer wall of the hollow guidewire sheath 268. The tubular sheath 274 is secured at its proximal end 276 to the hollow guidewire sheath guidewire 268. This may be accomplished through any of a variety of securing techniques, such as heat shrinking, thermal bonding, adhesives, mechanical interfit and the like. In one embodiment, the hollow guidewire sheath 268 is provided with an annular ridge recess, one or more projections, or other diameter enlarging or modifying structures 278 to provide an interference fit with the proximal end 276 of the tubular sheath 274, and then the proximal end 276 of the tubular sheath is heat shrunk and/or bonded to the retention structure 278 of the hollow guidewire sheath 268 to provide a secure connection. Any of a variety of other techniques for providing a secure connection between the hollow guidewire sheath 268 and tubular sheath 274 can readily be used in the context of the present invention as will be apparent to those of skill in the art in view of the disclosure herein.

In certain embodiments, the tubular sheath 274 is spaced at least about 6 cm, often between about 6-12 cm, and generally between about 8-10 cm from the distal end 271 of the hollow guidewire sheath 268. In general, the tubular sheath 274 is positioned on the hollow guidewire such that the distal end of the hollow guidewire sheath 268 has sufficient length to extend beyond the tubular sheath 274 and through the lumen of the main graft portion when a branch graft portion is constrained within the tubular sheath 274, thus the spacing of the tubular sheath 274 on the hollow guidewire sheath 268 will depend upon the length of the main graft portion of the implant. In certain embodiments, the distal end of the hollow guidewire sheath may be sized to extend to the end of the main graft portion. Alternatively, the distal end 271 of the hollow guidewire assembly may be sized to extend slightly beyond the end of the main graft portion. In use, when the hollow guidewire sheath 268 is proximally retracted, the tubular sheath 274 will also be proximally retracted, thereby releasing a constrained contralateral graft portion from the open end of the tubular sheath 274. The hollow guide wire sheath 268 and/or the attachment between the hollow guidewire sheath 268 and the branch graft restraint mechanism 274 may further be provided with one or more radiopaque markers 280, such as a gold marker, to facilitate visualization during placement. The foregoing dimensions and materials can be varied widely as will be appreciated by those of skill in the art in view of the desired performance characteristics and manufacturing techniques.

In certain embodiments, the branch graft restraint mechanism may alternatively comprise a pull ribbon, a belt or a wire configured to be wrapped around a branch graft portion to constrain the branch graft portion, a peelable sheath as disclosed in co-pending U.S. patent application Ser. No. 11/522, 292, entitled "MULTI-SEGMENTED GRAFT DEPLOYMENT SYSTEM" and filed on Sep. 15, 2006, hereby incorporated by reference in its entirety, or any other suitable restraint mechanism known in the arts.

Figure 9:
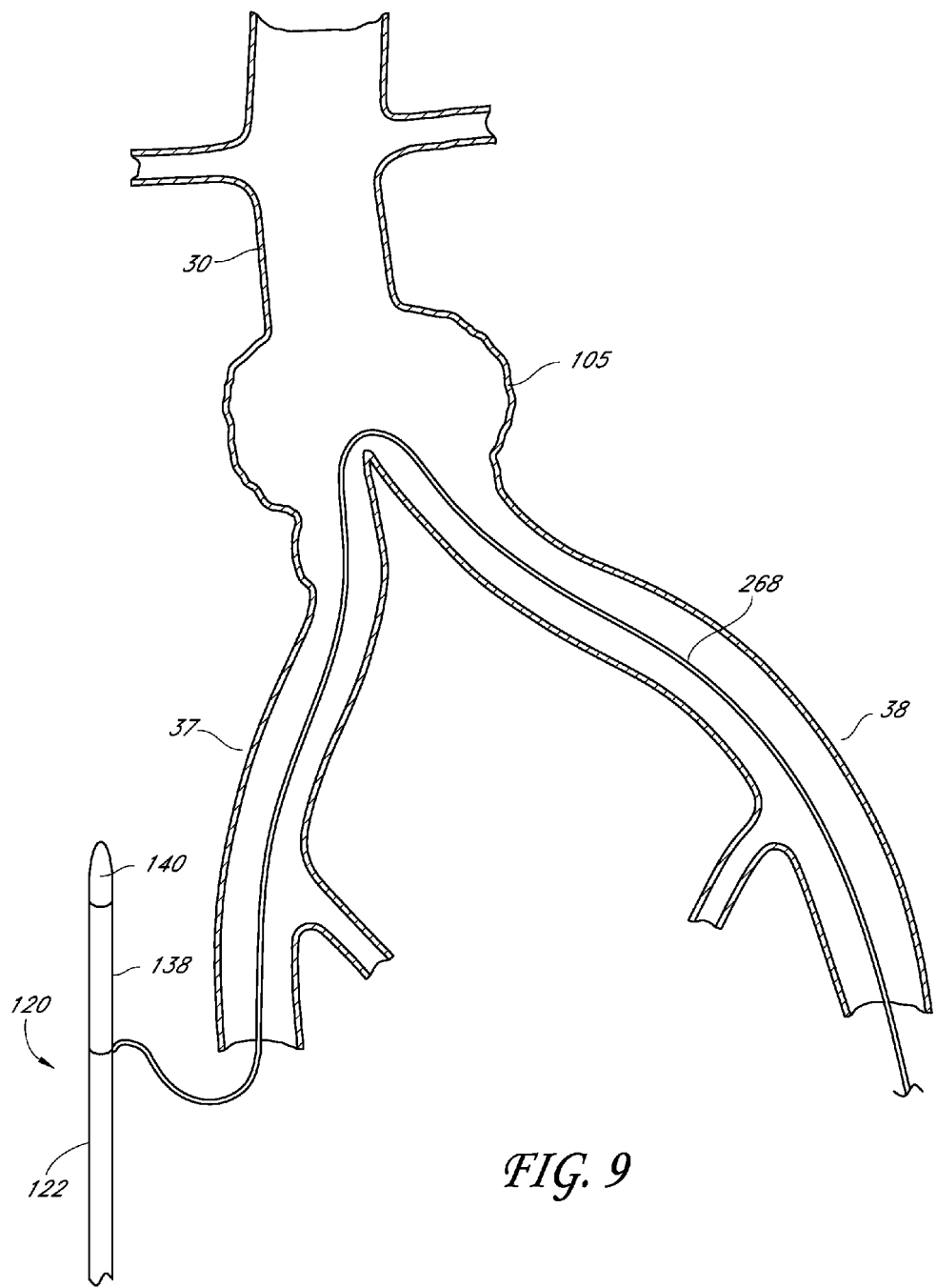
FIG. 9 is a schematic representation of an embodiment of the deployment catheter with the dual concentric guidewire assembly positioned across the bifurcation and within the contralateral iliac.

In use, the guidewire assembly 266 may be used in conjunction with a deployment catheter such as deployment catheter 120 to deliver and deploy a bifurcated prosthesis in a patient's aorta while leaving a guidewire positioned through the bifurcated prosthesis after the graft has been fully deployed. Referring to FIG. 9, the hollow guidewire sheath 268 is introduced into the ipsilateral iliac through an ipsilateral access site in the femoral artery, advanced superiorly towards the aorta, and using cross-over techniques known to those skilled in the arts, subsequently advanced inferiorly down the contralateral iliac and out a contralateral access site in the contralateral femoral artery. A tubular sheath 274 near the distal end of the hollow guidewire sheath 268 constrains a branch graft portion 156 of a graft 150 contained within a deployment catheter 120. The distal end of the hollow guidewire sheath 268 extends beyond the tubular sheath 274 and through the lumen of a compressed main graft portion 152 of the graft 150. Thus, the distal end of the hollow guidewire sheath 268 is effectively attached to the deployment catheter 120 while the proximal end of the hollow guidewire sheath extends from the contralateral access site.

Figure 10:
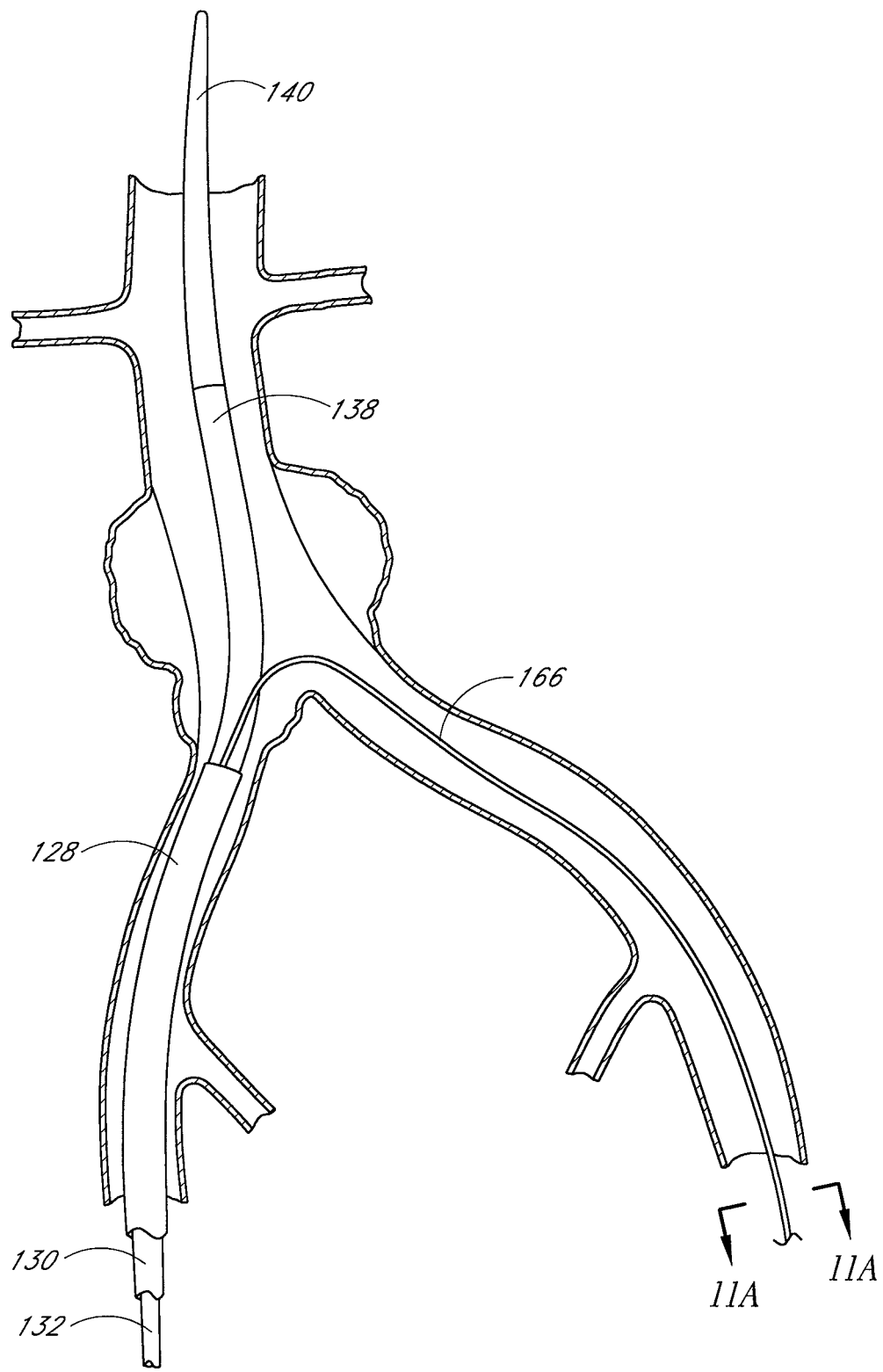
FIG. 10 is a schematic representation as in FIG. 9, with the deployment catheter positioned in the aorta.

Referring to FIG. 10, once the hollow guidewire sheath 268 has been positioned across the bifurcation in the aorta, the deployment catheter 120 is advanced over a second guidewire, such as a standard 0.035 inch guidewire from the ipsilateral access site into the aorta using techniques known to those skilled in the arts. Traction is applied to the hollow guidewire sheath 268 from the contralateral access site to take up the slack in the hollow guidewire sheath 268 as the deployment catheter 120 is advanced into the aorta.

Figure 11B:
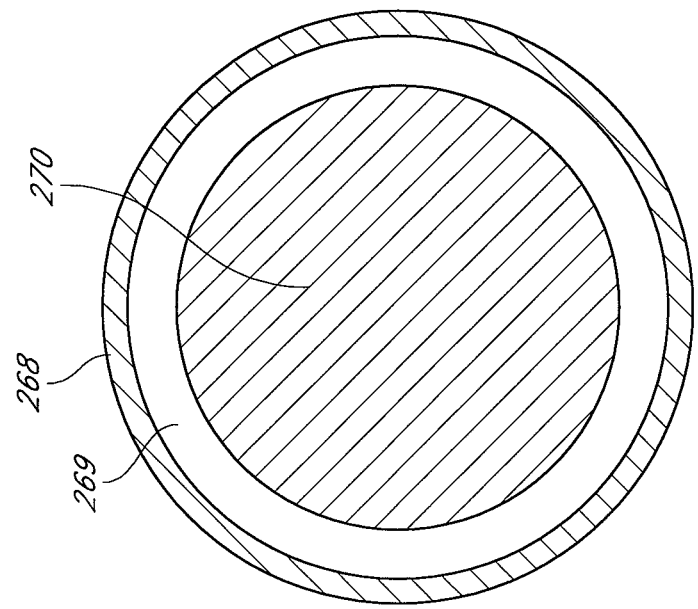
FIG. 11B is a cross-sectional view of the dual concentric guidewire assembly with the core wire advanced therethrough once the catheter has been positioned in the aorta in FIG. 10.
Figure 11A:
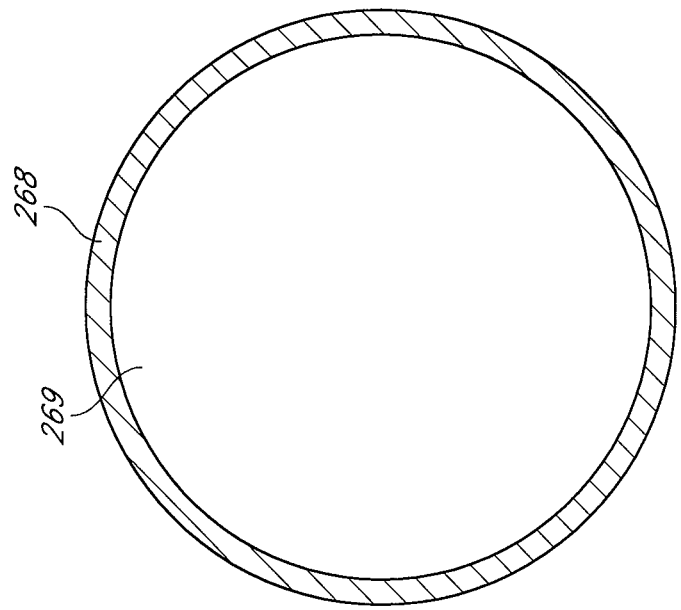
FIG. 11A is a cross-sectional view of the dual concentric guidewire assembly as initially positioned in the contralateral iliac in FIG. 9.

As shown in FIG. 11A, at this time, the central lumen 269 of the hollow guidewire sheath 268 may be empty. The hollow guidewire sheath 268 has been positioned across the bifurcation and the deployment catheter 120 has been advanced into the aorta over a second guidewire without the inner core wire being positioned in the hollow guidewire sheath 268. Once the deployment catheter 120 is positioned within the patient's aorta, an inner core wire 270 is advanced superiorly from the contralateral access site through the central lumen 269 of the hollow guidewire sheath 268 until the point where the hollow guidewire sheath 268 enters the deployment catheter 120, i.e. the junction 131 between the outer sheath 128 of the deployment catheter and the outer tubular housing 138 that constrains the main graft portion as shown in FIG. 4. FIG. 11B shows a cross-section of the hollow guidewire sheath 268 with the inner core wire 270 slidably inserted in the central lumen 269 of the hollow guidewire sheath 268.

Figure 12:
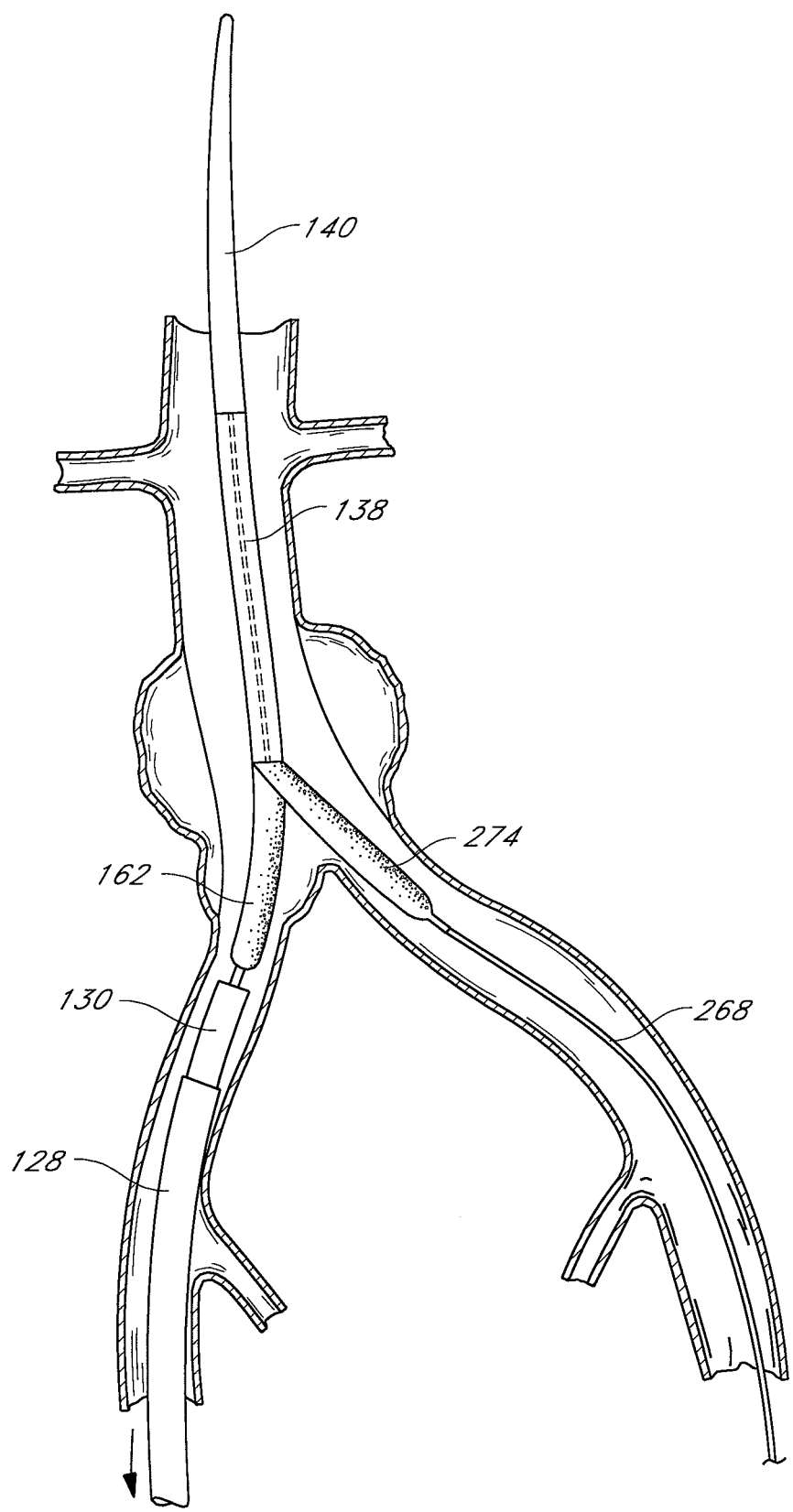
FIG. 12 is a schematic representation as in FIG. 10, with the compressed iliac branches of the graft positioned within the iliac arteries.

Referring to FIG. 12, the outer sheath 128 of the deployment catheter 120 may then be proximally retracted to expose the constrained iliac branches 154 and 156 of the bifurcated graft. The main graft portion 152 remains constrained by a proximally extending tubular housing 138 attached to the distal tip 140 of the deployment catheter 120 while the iliac branches of the graft remain compressed within separate branch graft restrain mechanisms, such as an ipsilateral tubular sheath 162 attached to the central core of the deployment catheter 120 and the contralateral tubular sheath 274 attached to the hollow guidewire sheath 268. The deployment catheter 120 is then proximally retracted such that the compressed ipsilateral and contralateral branch graft portions rest on or in the vicinity of the bifurcation of the aorta and extend into their respective branch iliacs.

Figure 13:
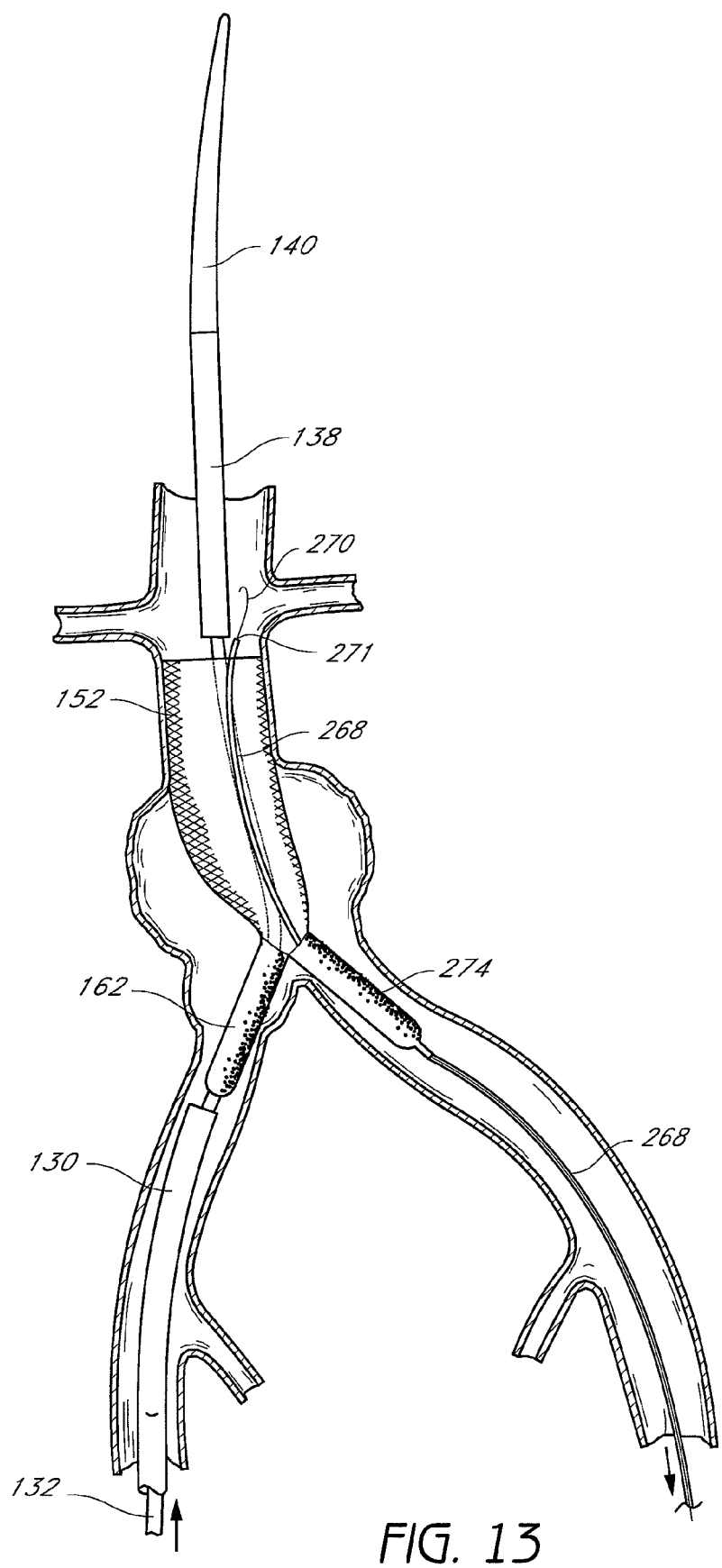
FIG. 13 is a schematic representation as in FIG. 12, with the main graft portion of the graft deployed within the aorta with the guidewire assembly extending through the expanded main graft portion.

Referring to FIG. 13, the main graft portion 152 is then deployed from the deployment catheter 120, for example, as discussed above, by distally advancing a distal tubular extrusion 138 of the deployment catheter 120 which constrains the self-expanding main graft portion 152. Once the main graft portion 152 has been expanded, the inner core wire 270 may be further advanced superiorly through the distal end of the hollow guidewire sheath 268 which extends through the lumen of the main graft portion 152. Because the distal end the hollow guidewire sheath 268 extends beyond the tubular sheath 174 through the main graft portion, the tip of the inner core wire 270 will not catch on the endoskeleton of the expanded main graft portion 152 as it is advanced distally through the lumen of the main graft portion. Instead, the inner core wire 270 may be advanced through the distal end of the hollow guidewire sheath 268 such that when the hollow guidewire sheath 268 is withdrawn, the inner core wire will remain positioned through the central lumen of the expanded main graft portion 152 to provide subsequent access to the main graft as well as superiorly within the patient's aorta.

Figure 14:
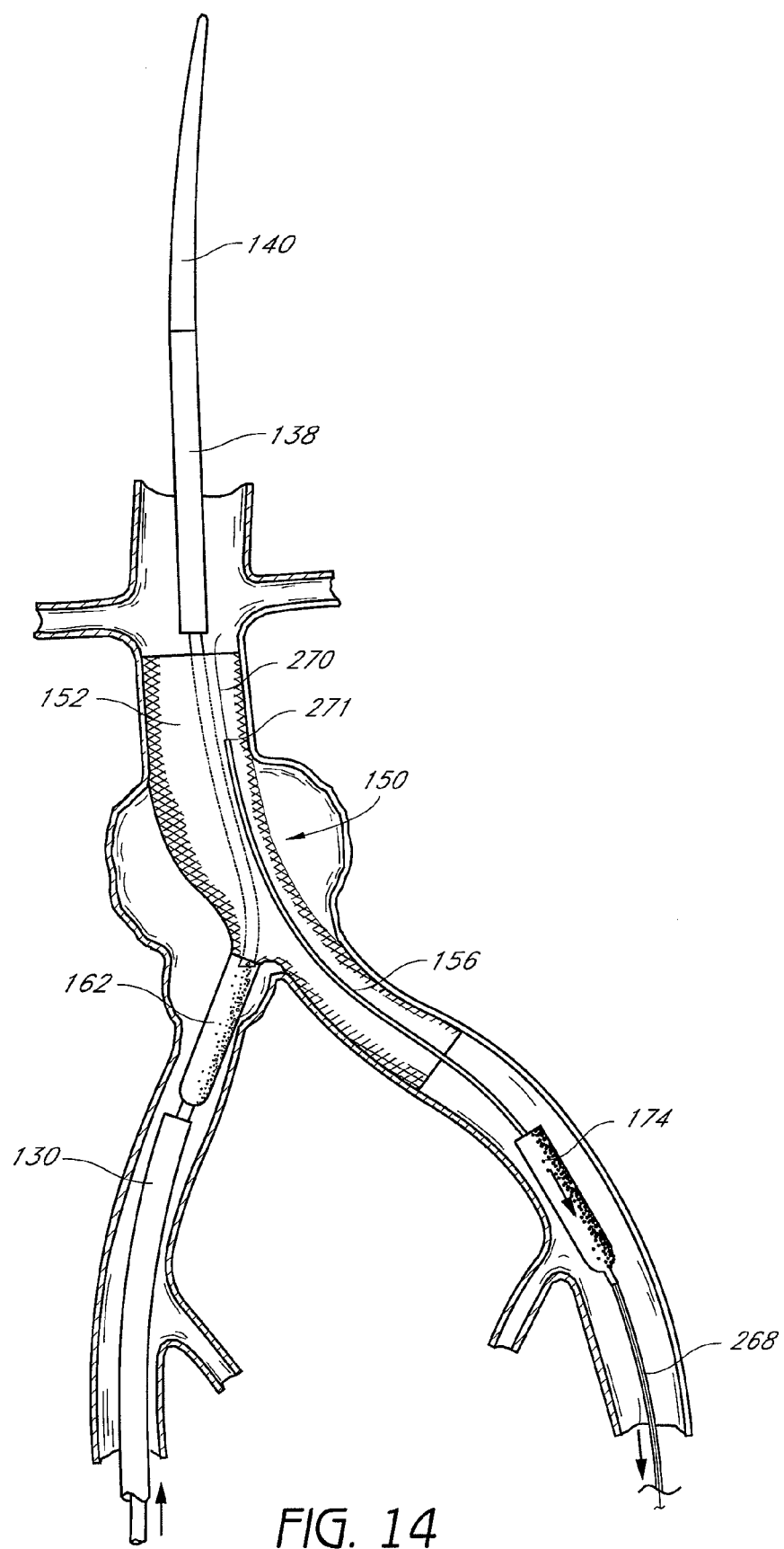
FIG. 14 is a schematic representation as in FIG. 13, following proximal retraction of the outer tubular sheath of the guidewire assembly and deployment of the contralateral graft portion.

Referring to FIG. 14, the hollow guidewire sheath 268 is pulled proximally through the contralateral access site to withdraw the hollow guidewire sheath 268 and branch restraint mechanism 274 carried by the hollow guidewire sheath 268, thereby deploying the contralateral branch portion of the graft 156. The inner core wire 270 is left in position through the expanded contralateral branch graft portion 156 and main graft portion 152 for allowing subsequent access to the patient's aorta and the expanded graft. As discussed above, the inner core wire 270 has a length at least twice as long as the hollow guidewire sheath 268 such that physical contact can be maintained with the inner core wire 270 while the hollow guidewire sheath 268 is being withdrawn over the inner core wire 270 to prevent the friction between the inner core wire 270 and the hollow guidewire sheath 268 from also withdrawing the inner core wire 270.

Figure 15:
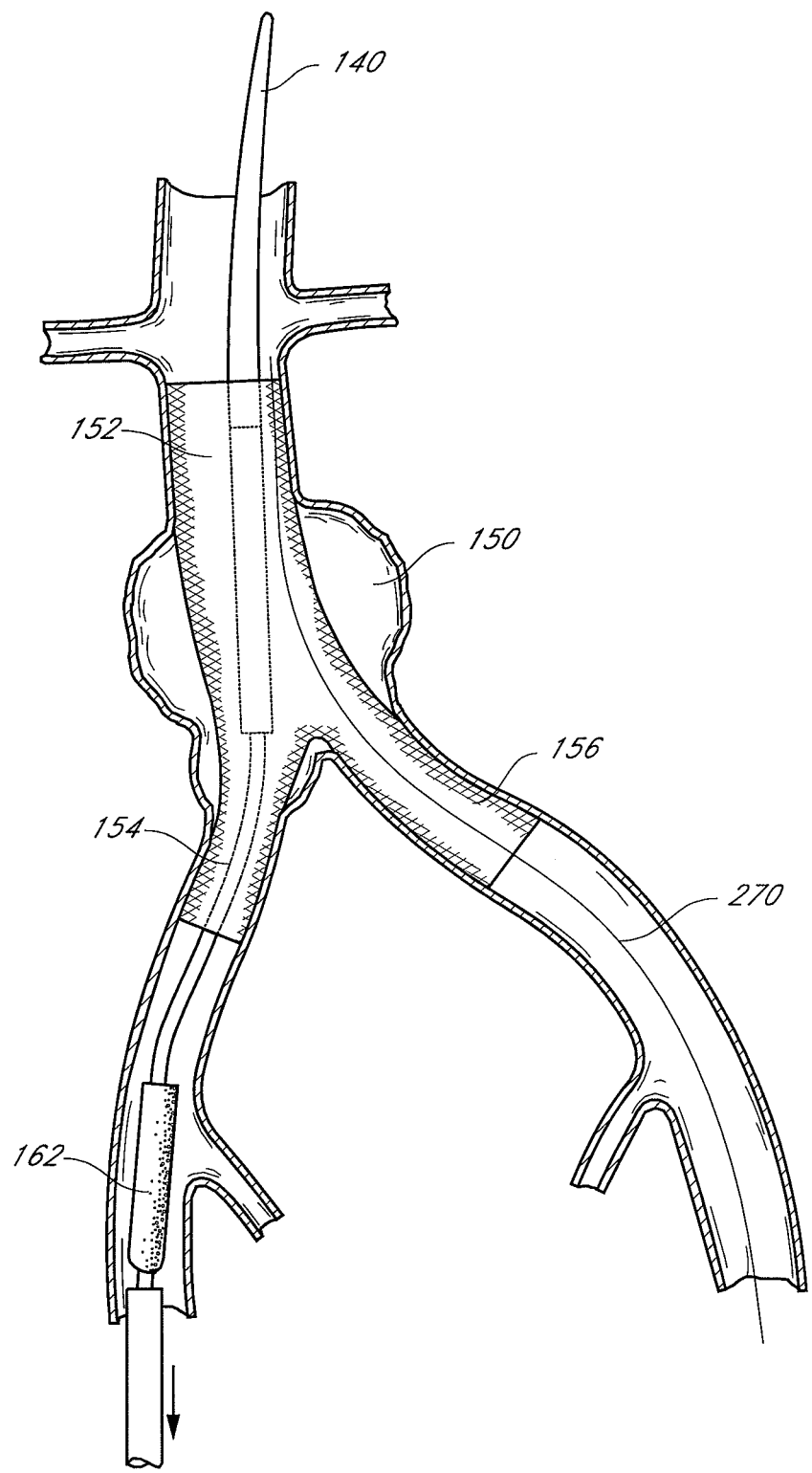
FIG. 15 is a schematic representation as in FIG. 14 following deployment of the ipsilateral branch graft portion.

Referring to FIG. 15, the ipsilateral tubular sheath 162 may then be retracted to deploy a self expanding ipsilateral branch graft portion 154. Once the ipsilateral branch portion 154 has been expanded, the deployment catheter 120 may then be proximally retracted through the expanded main graft portion 152 and ipsilateral branch graft portion 154 and withdrawn from the patient through the ipsilateral access site.

Figure 16:
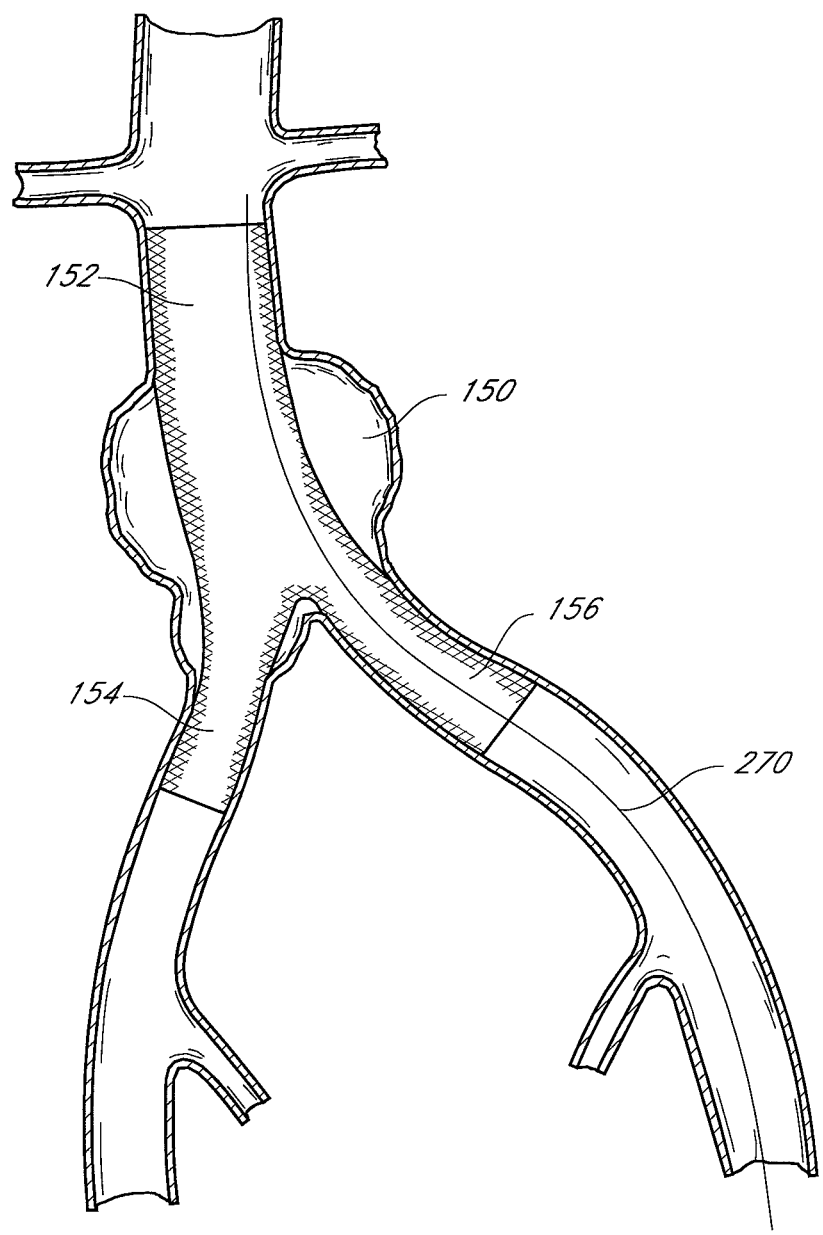
FIG. 16 is a schematic representation as in FIG. 15, of the deployed bifurcated graft with the inner core wire positioned within the main graft portion of the deployed graft.

As shown in FIG. 16, the inner core wire 270 remains positioned in the patient's aorta, providing continued access to the graft and the aorta through the contralateral iliac. Thus, any variety of diagnostic and/or therapeutic procedures may be accomplished following the implantation of the bifurcated graft and that require guidance can use the inner core wire 270. For example, the inner core wire 270 may be used to guide a balloon dilation catheter to the graft site to dilate a stenosis, re-expand a portion of the graft or perform other touch up procedures. Alternatively, the inner core wire may be used to guide a subsequent catheter to the graft location for deploying a cuff either in the aorta, for example at the distal end of the main graft segment, or alternatively in the iliac artery at the proximal end of one of the branch graft portions. In addition or in the alternative, those of skill in the art will recognize that a variety of other therapeutic and/or diagnostic catheters or instruments that require guidance can also utilize the inner core 270.

For certain post-implantation procedures, the catheters, such as the dilation catheter or cuff deployment catheter described above, may be configured to be advanced over a smaller diameter, more flexible wire such as the inner core wire. However, for certain devices, the smaller diameter of the inner core wire may not provide enough strength or stability to guide the catheter to the treatment site. For example, many catheters are currently designed to be delivered over a 0.035 inch guidewire, and thus an inner core wire which has a diameter of about 0.014 inches may not provide enough stability over which to guide the catheter.

In such cases, an exchange catheter having an inner diameter greater than the diameter of the desired guidewire may be advanced through the contralateral access site over the inner core wire 270. Once the exchange catheter has been advanced to the distal end of the inner core wire 270, the inner core wire 270 may be proximally retracted through the contralateral access site. A larger guidewire, such as a 0.035 inch guidewire may then be advanced through the exchange catheter to the main graft portion. Once the larger guidewire has been advanced through the exchange catheter, the exchange catheter may be proximally withdrawn from the contralateral access site, leaving the larger diameter guidewire in position in the patient's contralateral iliac and extending through the main graft portion. Thus, the smaller diameter inner core wire may be exchanged for a larger diameter guidewire more suitable for use with larger instrument catheters without encountering any of the complications associated with trying to advance a guidewire having a curved distal tip through a deployed graft portion.

The exchange catheter may comprise an elongate flexible tubular body having a single lumen with an inside diameter of at least about 0.003 inches greater than the outer diameter of the desired procedure guidewire. The body may include a helical coil, braid, or weave within the tubular wall, to resist kinking, as is understood in the art. A proximal hub may be provided on the tubular body, to facilitate grasping and removal of the exchange catheter following placement of the desired procedure guidewire.

Although the foregoing description of the preferred embodiments of the present invention has shown, described and pointed out the fundamental novel features of the invention, it will be understood that various omissions, substitutions, and changes in the form of the detail of the apparatus as illustrated as well as the uses thereof, may be made by those skilled in the art, without departing from the spirit of the invention. For example, while the delivery system is described with respect to deploying a bifurcated stent in the abdominal aortic and leaving a guidewire positioned through the expanded stent, it is further envisioned that the delivery system could be used to deliver a prosthesis having a main portion and at least one branch portion, or alternatively a prosthesis having only a straight, main graft portion, to other branched intravascular vessels (e.g., the thoracic aorta and a cardiac artery) and leave a guidewire positioned through the expanded prosthesis.

What is claimed is:

1. A self-expandable endoluminal vascular prosthesis deployment system, comprising:
    an endoluminal vascular prosthesis having at least a main graft portion having a lumen therethrough and a first branch graft portion having a lumen therethrough;
    a deployment catheter having a catheter body for deploying the endoluminal vascular prosthesis, said deployment catheter having a central tubular core having a guidewire lumen extending therethrough, and distal and proximal ends, wherein said first branch graft portion is constrained within a branch graft restraint member comprising a tubular sheath prior to deployment;
    a contralateral guidewire extending through the first branch graft portion and the branch graft restraint member in a predeployment state; and
    an inner core member slidably positionable within said contralateral guidewire;
    wherein:
        said contralateral guidewire comprises a hollow guidewire securely connected to said branch graft restraint member such that movement of the hollow guidewire and branch graft restraint member connected thereto away from the main graft portion simultaneously moves the branch graft restraint member away from the main graft portion and releases said first branch graft portion from said branch graft restraint member;
        the hollow guidewire comprises a distal end portion that extends through the lumen of the first branch graft portion and substantially into the lumen of the main graft portion in a predeployment state; and
        the hollow guidewire has a substantially uniform cross-sectional size and shape along an entire the length thereof, and has a proximal end portion that is advanceable through a patient's vasculature.

2. The deployment system of claim 1, wherein the branch graft restraint member is located near the distal end of the hollow guidewire.

3. The deployment system of claim 1, wherein the tubular sheath is mounted to an outer wall of the hollow guidewire.

4. The deployment system of claim 1, wherein the inner core member is substantially longer than the hollow guidewire.

5. The deployment system of claim 4, wherein the inner core member has a length between about 2-3 times greater than a length of the hollow guidewire.

6. The deployment system of claim 5, wherein the hollow guidewire has a length of between about 120-140 cm and the inner core member has a length of between about 240-300 cm.

7. The deployment system of claim 1, wherein the hollow guidewire comprises a reinforced tubular member.

8. The deployment system of claim 7, wherein the hollow guidewire comprises a composite tubular member comprising a polyimide tube over a wire coil wrapped around the polyimide tube.

9. The deployment system of claim 1, wherein the distal end portion of the hollow guidewire is supported within a tubular member of the deployment catheter in a pre-deployment state and the remainder of the length of the hollow guidewire is positioned outside the tubular member in the pre-deployment state.

10. The deployment system of claim 1, wherein the deployment catheter further comprises a tubular member having proximal and distal end portions, and the hollow guidewire does not extend through the entire tubular member such that only the distal end portion of the tubular member surrounds the hollow guidewire when the deployment catheter is in a pre-deployment state.

11. The deployment system of claim 1, wherein:
the deployment catheter further comprises a tubular member projecting from a proximal portion of the deployment catheter;
the tubular member is moveable between a first position wherein a distal end portion of the tubular member axially surrounds at least a portion of the first branch graft portion of the prosthesis and a second position wherein a distal end portion of the tubular member is proximal to a proximal end portion of the first branch graft portion of the prosthesis; and
when the tubular member is in the second position, proximal movement of the hollow guidewire will result in proximal movement of the branch graft restraint member.

12. The deployment system of claim 11, wherein the hollow guidewire does not pass through a proximal end portion of the tubular member.

13. The deployment system of claim 1, wherein the hollow guidewire is independently moveable relative to the catheter body.

14. The deployment system of claim 1, wherein only a distal portion of the hollow guidewire is positioned within the deployment catheter and wherein a proximal and an intermediate portion of the hollow guidewire are moveable relative to the deployment catheter.

15. A self-expandable endoluminal vascular prosthesis deployment system, comprising:
an endoluminal vascular prosthesis having at least a main graft portion having a lumen therethrough and a first branch graft portion having a lumen therethrough;
a deployment catheter having a catheter body for deploying the endoluminal vascular prosthesis, said deployment catheter having a central tubular core having a guidewire lumen extending therethrough, and distal and proximal ends, wherein said first branch graft portion is constrained within a branch graft restraint member comprising a tubular sheath prior to deployment;
a contralateral guidewire extending through the first branch graft portion and the branch graft restraint tubular sheath in a predeployment state; and
an inner core member slidably positionable within said contralateral guidewire;
wherein:
said contralateral guidewire comprises a hollow guidewire securely connected to said branch graft restraint member such that movement of the hollow guidewire and branch graft restraint connected thereto away from the main graft portion simultaneously moves the branch graft restraint member away from the main graft portion and releases said branch graft from said branch graft restraint member;
the hollow guidewire comprises a distal end portion that extends through the lumen of the first branch graft portion and substantially into the lumen of the main graft portion in a predeployment state; and
a proximal end portion of the hollow guidewire is sized and configured to be advanceable through a first puncture site in the body and withdrawn through a second puncture site.

16. The deployment system of claim 15, wherein the tubular sheath is mounted to an outer wall of the hollow guidewire.

17. The deployment system of claim 15, wherein the inner core member has a length between about 2-3 times greater than a length of the hollow guidewire.

18. The deployment system of claim 15, wherein the hollow guidewire comprises a composite tubular member comprising a polyimide tube over a wire coil wrapped around the polyimide tube.

19. The deployment system of claim 15, wherein the distal end portion of the hollow guidewire is supported within a tubular member of the deployment catheter in a pre-deployment state and the remainder of the length of the hollow guidewire is positioned outside the tubular member in the pre-deployment state.

20. The deployment system of claim 15, wherein the deployment catheter further comprises a tubular member having proximal and distal end portions, and the hollow guidewire does not extend through the entire tubular member such that only the distal end portion of the tubular member surrounds the hollow guidewire when the deployment catheter is in a pre-deployment state.

21. The deployment system of claim 15, wherein:
the deployment catheter further comprises a tubular member projecting from a proximal portion of the deployment catheter;
the tubular member is moveable between a first position wherein a distal end portion of the tubular member axially surrounds at least a portion of the first branch graft portion of the prosthesis and a second position wherein a distal end portion of the tubular member is proximal to a proximal end portion of the first branch graft portion of the prosthesis; and
when the tubular member is in the second position, proximal movement of the hollow guidewire will result in proximal movement of the branch graft restraint member.

22. The deployment system of claim 21, wherein the hollow guidewire does not pass through the proximal end portion of the tubular member.

* * * * *